United States Patent
Hovda et al.

(10) Patent No.: US 6,363,937 B1
(45) Date of Patent: *Apr. 2, 2002

(54) SYSTEM AND METHODS FOR ELECTROSURGICAL TREATMENT OF THE DIGESTIVE SYSTEM

(75) Inventors: David C. Hovda, Mountain View; Hira V. Thapliyal, Los Altos, both of CA (US); Philip E. Eggers, Dublin, OH (US)

(73) Assignee: ArthroCare Corporation, Sunnyvale, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/074,020

(22) Filed: May 6, 1998

Related U.S. Application Data

(63) Continuation-in-part of application No. 08/990,374, filed on Dec. 15, 1997, now Pat. No. 6,109,268, which is a continuation-in-part of application No. 08/485,219, filed on Jun. 7, 1995, now Pat. No. 5,697,281.

(51) Int. Cl.[7] ............................................. A61B 19/00
(52) U.S. Cl. .......................... 128/898; 606/41; 607/133
(58) Field of Search .............................. 606/41, 42, 45, 606/46, 48, 56; 607/101, 102, 116, 133; 128/898

(56) References Cited

U.S. PATENT DOCUMENTS

| | | |
|---|---|---|
| 2,050,904 A | 8/1936 | Trice |
| 4,033,351 A | 7/1977 | Hetzel |
| 4,040,426 A | 8/1977 | Morrison, Jr. |
| 4,043,342 A | 8/1977 | Morrison, Jr. |
| 4,116,198 A | 9/1978 | Roos |
| 4,184,492 A | 1/1980 | Meinke et al. |
| 4,202,337 A | 5/1980 | Hren et al. |
| 4,228,800 A | 10/1980 | Degler, Jr. et al. |

(List continued on next page.)

FOREIGN PATENT DOCUMENTS

| | | |
|---|---|---|
| EP | 0703461 | 3/1996 |
| EP | 0740926 | 11/1996 |
| EP | 0754437 | 1/1997 |
| GB | 2308979 | 7/1997 |

(List continued on next page.)

OTHER PUBLICATIONS

C. Slager et al. (1987) *Z. Kardiologie* 76(6) :67–71.
C. Slager et al. (1985) *JACC* 5 (6):1382–6.
P. Nardella (1989) *SPIE* 1068: 42–49.
Elsasser et al. (1976) *Medizinal–Markt/Acta Medicotechnica* 24 (4):129–134.
E. Kramolowsky et al. (1991) J. of Urology 146:669–674.

(List continued on next page.)

*Primary Examiner*—Michael Peffley
(74) *Attorney, Agent, or Firm*—John T. Raffle

(57) ABSTRACT

The present invention provides systems and methods for selectively applying electrical energy to a target location within the gastrointestinal tract, such as the lower esophageal sphincter (LES). In one aspect of the invention, high frequency voltage is applied between the electrode terminal (s) and one or more return electrode(s) to remove a small tissue segment, channel or hole from the region near or in the LES to shrink the turbinates and prevent swelling, due to the formation of scar tissue as the wound heals. The high frequency voltage may be selected to effect a small amount of thermal damage to the walls of the channel or hole to facilitate the formation of scar tissue without extending this thermal damage beyond the immediate region of the target site. In another aspect, the high frequency voltage is selected to contract collagen fibers within the LES to improve its tone, thereby reducing the frequency of reflux.

7 Claims, 16 Drawing Sheets

U.S. PATENT DOCUMENTS

| | | |
|---|---|---|
| 4,232,676 A | 11/1980 | Herczog |
| 4,248,231 A | 2/1981 | Herczog et al. |
| 4,326,529 A | 4/1982 | Doss et al. |
| 4,381,007 A | 4/1983 | Doss |
| 4,476,862 A | 10/1984 | Pao |
| 4,532,924 A | 8/1985 | Auth et al. |
| 4,548,207 A | 10/1985 | Reimels |
| 4,567,890 A | 2/1986 | Ohta et al. |
| 4,593,691 A | 6/1986 | Lindstrom et al. |
| 4,674,499 A | 6/1987 | Pao |
| 4,682,596 A | 7/1987 | Bales et al. |
| 4,706,667 A | 11/1987 | Roos |
| 4,765,331 A | 8/1988 | Petruzzi et al. |
| 4,823,791 A | 4/1989 | D'Amelio |
| 4,860,752 A | 8/1989 | Turner |
| 4,931,047 A | 6/1990 | Broadwin et al. |
| 4,936,301 A | 6/1990 | Rexroth et al. |
| 4,943,290 A | 7/1990 | Rexroth et al. |
| 4,967,765 A | 11/1990 | Turner et al. |
| 4,976,711 A | 12/1990 | Parins et al. |
| 4,979,948 A | 12/1990 | Geddes et al. |
| 4,998,933 A | 3/1991 | Eggers et al. |
| 5,007,908 A | 4/1991 | Rydell |
| 5,009,656 A | 4/1991 | Reimels |
| 5,035,696 A | 7/1991 | Rydell |
| 5,057,105 A | 10/1991 | Malone et al. |
| 5,057,106 A | 10/1991 | Kasevich et al. |
| 5,078,717 A | 1/1992 | Parins et al. |
| 5,080,660 A | 1/1992 | Buelna |
| 5,083,565 A | 1/1992 | Parins |
| 5,098,431 A | 3/1992 | Rydell |
| 5,108,391 A | 4/1992 | Flachenecker et al. |
| 5,112,330 A | 5/1992 | Nishigaki et al. |
| 5,122,138 A | 6/1992 | Manwaring |
| 5,125,928 A | 6/1992 | Parins et al. |
| 5,178,620 A | 1/1993 | Eggers et al. |
| 5,190,517 A | 3/1993 | Zieve et al. |
| 5,192,280 A | 3/1993 | Parins |
| 5,195,959 A | 3/1993 | Smith |
| 5,196,007 A | 3/1993 | Ellman et al. |
| 5,197,963 A | 3/1993 | Parins |
| 5,217,457 A | 6/1993 | Delahuerga et al. |
| 5,249,585 A | 10/1993 | Turner |
| 5,267,994 A | 12/1993 | Gentelia et al. |
| 5,267,997 A | 12/1993 | Farin et al. |
| 5,273,524 A | 12/1993 | Fox et al. |
| 5,277,201 A | 1/1994 | Stern |
| 5,281,216 A | 1/1994 | Klicek |
| 5,281,218 A | 1/1994 | Imran |
| 5,290,282 A | 3/1994 | Casscells |
| 5,300,069 A | 4/1994 | Hunsberger et al. |
| 5,312,400 A | 5/1994 | Bales et al. |
| 5,314,406 A | 5/1994 | Arias et al. |
| 5,324,254 A | 6/1994 | Phillips |
| 5,330,470 A | 7/1994 | Hagen |
| 5,334,140 A | 8/1994 | Phillips |
| 5,334,183 A | 8/1994 | Wuchinich |
| 5,336,220 A | 8/1994 | Ryan et al. |
| 5,342,357 A | 8/1994 | Nardella |
| 5,366,443 A | 11/1994 | Eggers et al. |
| 5,370,675 A | 12/1994 | Edwards et al. |
| 5,380,277 A | 1/1995 | Phillips |
| 5,383,876 A | 1/1995 | Nardella |
| 5,383,917 A | 1/1995 | Desai et al. |
| 5,395,312 A | 3/1995 | Desai |
| 5,395,368 A | 3/1995 | Ellman et al. |
| 5,403,311 A * | 4/1995 | Abele et al. .................. 606/49 |
| 5,417,687 A | 5/1995 | Nardella et al. |
| 5,419,767 A | 5/1995 | Eggers et al. |
| 5,423,812 A | 6/1995 | Ellman et al. |
| 5,441,499 A | 8/1995 | Fritzsch |
| 5,454,809 A | 10/1995 | Janssen |
| 5,456,662 A | 10/1995 | Edwards et al. |
| 5,490,850 A | 2/1996 | Ellman |
| 5,505,728 A | 4/1996 | Ellman et al. |
| 5,514,130 A | 5/1996 | Baker |
| 5,556,397 A | 9/1996 | Long et al. |
| 5,562,503 A | 10/1996 | Ellman et al. |
| 5,562,703 A | 10/1996 | Desai |
| 5,569,242 A | 10/1996 | Lax et al. |
| 5,571,101 A | 11/1996 | Ellman et al. |
| 5,584,872 A | 12/1996 | LaFontaine et al. |
| 5,609,151 A | 3/1997 | Mulier et al. |
| 5,624,439 A | 4/1997 | Edwards et al. |
| 5,630,812 A | 5/1997 | Ellman et al. |
| 5,647,869 A | 7/1997 | Goble |
| 5,662,680 A | 9/1997 | Desai |
| 5,674,191 A | 10/1997 | Edwards et al. |
| 5,676,693 A | 10/1997 | LaFontaine |
| 5,681,282 A | 10/1997 | Eggers et al. |
| 5,683,366 A | 11/1997 | Eggers et al. |
| 5,683,386 A | 11/1997 | Ellman et al. |
| 5,683,387 A | 11/1997 | Garito |
| 5,695,495 A | 12/1997 | Ellman et al. |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,700,262 A | 12/1997 | Acosta |
| 5,707,349 A | 1/1998 | Edwards |
| 5,718,702 A | 2/1998 | Edwards |
| 5,725,524 A | 3/1998 | Mulier et al. |
| 5,733,282 A | 3/1998 | Ellman et al. |
| 5,738,114 A | 4/1998 | Edwards |
| 5,749,869 A | 5/1998 | Lindenmeier |
| 5,766,153 A | 6/1998 | Eggers et al. |
| 5,775,338 A | 7/1998 | Hastings |
| 5,800,379 A | 9/1998 | Edwards |
| 5,800,429 A | 9/1998 | Edwards |
| 5,807,395 A | 9/1998 | Mulier et al. |
| 5,810,764 A | 9/1998 | Eggers et al. |
| 5,817,049 A | 10/1998 | Edwards |
| 5,820,580 A | 10/1998 | Edwards et al. |
| 5,823,197 A | 10/1998 | Edwards |
| 5,827,277 A | 10/1998 | Edwards |
| 5,843,021 A | 12/1998 | Edwards et al. |
| 5,843,077 A | 12/1998 | Edwards |
| 5,885,277 A | 3/1999 | Korth |
| 5,897,553 A | 4/1999 | Mulier et al. |
| 5,921,983 A | 7/1999 | Shannon, Jr. |
| 5,944,715 A | 8/1999 | Goble et al. |
| 6,004,319 A | 12/1999 | Goble et al. |
| 6,006,755 A * | 12/1999 | Edwards ..................... 128/898 |
| 6,009,877 A * | 1/2000 | Edwards ..................... 128/898 |
| 6,013,076 A | 1/2000 | Goble et al. |
| 6,015,406 A | 1/2000 | Goble et al. |
| 6,027,501 A | 2/2000 | Goble et al. |
| 6,039,734 A | 3/2000 | Goble et al. |
| 6,044,846 A * | 4/2000 | Edwards ..................... 128/898 |
| 6,056,746 A | 5/2000 | Goble et al. |
| 6,068,628 A | 5/2000 | Fanton et al. |
| 6,073,052 A * | 6/2000 | Zelickson et al. .......... 607/100 |
| 6,074,386 A | 6/2000 | Goble et al. |
| 6,090,106 A | 7/2000 | Goble et al. |
| 6,093,186 A | 7/2000 | Goble |

FOREIGN PATENT DOCUMENTS

| | | |
|---|---|---|
| GB | 2308980 | 7/1997 |

| | | |
|---|---|---|
| GB | 2308981 | 7/1997 |
| GB | 2327350 | 1/1999 |
| GB | 2327351 | 1/1999 |
| GB | 2327352 | 1/1999 |
| JP | 57-117843 | 7/1982 |
| WO | WO 90/07303 | 7/1990 |
| WO | WO 92/21278 | 12/1992 |
| WO | 93/20747 | 10/1993 |
| WO | 94/04220 | 3/1994 |
| WO | 94/08654 | 4/1994 |
| WO | 96/00042 | 1/1996 |
| WO | 97/00646 | 1/1997 |
| WO | 97/00647 | 1/1997 |
| WO | 97/24073 | 7/1997 |
| WO | 97/24993 | 7/1997 |
| WO | 97/24994 | 7/1997 |
| WO | 97/30644 | 8/1997 |
| WO | 97/30645 | 8/1997 |
| WO | 97/30646 | 8/1997 |
| WO | 97/30647 | 8/1997 |
| WO | 97/41785 | 11/1997 |
| WO | 97/41786 | 11/1997 |
| WO | 97/41787 | 11/1997 |
| WO | 97/41788 | 11/1997 |
| WO | 97/43969 | 11/1997 |
| WO | 97/43970 | 11/1997 |
| WO | 97/43972 | 11/1997 |
| WO | 97/43973 | 11/1997 |
| WO | 97/44092 | 11/1997 |
| WO | 97/48346 | 12/1997 |
| WO | WO 98/27879 | 7/1998 |
| WO | 99/08613 | 2/1999 |
| WO | 99/35986 | 7/1999 |
| WO | 99/35987 | 7/1999 |
| WO | 99/35988 | 7/1999 |
| WO | 99/51155 | 10/1999 |
| WO | 99/51158 | 10/1999 |

OTHER PUBLICATIONS

R. Tucker et al. (1990) *Urol. Res.* 18:291–294.
R. Tucker et al. (1989) *J. of Urology* 141:662–665.
R. Tucker et al. (1989) Abstract P14–11, $7^{th}$ World Congress on Endourology and ESWL, Nov. 27–30, 1989, Kyoto, Japan.
Rand et al. (1985) *J. Arthro. Surg.* 1:242–246.
J. Pearce *Electrosurgery*, John Wiley & Sons, New York, 1986.

\* cited by examiner

SYSTEM AND METHODS FOR ELECTROSURGICAL TREATMENT OF THE DIGESTIVE SYSTEM

RELATED APPLICATIONS

The present invention is a continuation-in-part of U.S. patent application Ser. No. 08/990,374, filed Dec. 15, 1997, now U.S. Pat. No. 6,109,268, which is a continuation-in-part of U.S. patent application Ser. No. 08/485,219, filed on Jun. 7, 1995, now U.S. Pat. No. 5,697,281, the complete disclosures of which are incorporated herein by reference for all purposes.

The present invention is related to commonly assigned U.S. patent application Ser. No. 09/058,571, filed on Apr. 10, 1998, now U.S. Pat. No. 6,142,992 and U.S. patent application Ser. No. 09/054,323, filed on Apr. 2, 1998 now U.S. Pat. No. 6,063,079, U.S. patent application Ser. No. 09/010,382, filed Jan. 21, 1998 now U.S. Pat. No. 6,190,381, and U.S. patent application Ser. No. 09/032,375, filed Feb. 27, 1998, U.S. patent application Ser. No. 08/977,845, filed on Nov. 25, 1997 now U.S. Pat. No. 6,210,402, Ser. No. 08/942,580, filed on Oct. 2, 1997, now U.S. Pat. No. 6,159,194, Ser. No. 09/026,851, filed Feb. 20, 1998, now U.S. Pat. No. 6,277,112, U.S. application Ser. No. 08/753,227, filed on Nov. 22, 1996, now U.S. Pat. No. 5,873,855, U.S. application Ser. No. 08/687,792, filed on Jul. 18, 1996 now U.S. Pat. No. 5,843,019, and PCT International Application, U.S. National Phase Ser. No. PCT/US94/05168, filed on May 10, 1994, now U.S. Pat. No. 5,697,909, which was a continuation-in-part of U.S. patent application Ser. No. 08/059,681, filed on May 10, 1993, (now abandoned), which was a continuation-in-part of U.S. patent application Ser. No. 07/958,977, filed on Oct. 9, 1992, now U.S. Pat. No. 5,366,443 which was a continuation-in-part of U.S. patent application Ser. No. 07/817,575, filed on Jan. 7, 1992 (now abandoned), the complete disclosures of which are incorporated herein by reference for all purposes. The present invention is also related to commonly assigned U.S. Pat. No. 5,683,366, filed Nov. 22, 1995, the complete disclosure of which is incorporated herein by reference for all purposes.

BACKGROUND OF THE INVENTION

The present invention relates generally to the field of electrosurgery, and more particularly to surgical devices and methods which employ high frequency electrical energy to treat tissue in regions of the digestive tract and associated organs, such as the pharynx, esophagus, stomach, intestines, anorectum, liver, pancreas and the like. The present invention is particularly suited for treating the lower esophageal sphincter in patient's suffering from gastroesophageal reflux.

Gastroesophageal reflux, better known as heartburn or acid indigestion, occurs when the esophageal mucosa suffers prolonged exposure to noxious gastric acid and pepsin because of deficiencies of the esophageal reflux barrier and acid-clearing mechanisms. Normally, the hydrocholoric acid and protease pepsin that are present in the stomach are excluded from the esophagus by the valve action of the lower esophageal sphincter (LES). Weakness of LES tone or abnormally frequent relaxations of the LES allow gastric acid and pepsin to reflux into the esophagus and potentially damage the mucosa. Symptoms of gastroesophageal reflux disease include heartburn, regurgitation, chest pain (due to a spasm of the acid-bathed esophagus), coughing, hoarseness, sore throat, gingivitis and asthma.

Treatment of gastroesophageal reflux typically involves pharmaceuticals that either neutralize acids in the stomach, or prevent the secretion of gastric acid into the stomach. Often, the complete control of heartburn requires extremely aggressive acid suppression. These pharmaceuticals, however, do not treat the problem (i.e., a loose lower sphincter). In addition, it has been shown that reflux can produce a broncho-contriction (asthma-like symptoms) either through reflex (vagally induced from reflux in the esophagus) or reflux into the trachea. Changing the ph of the stomach acid does not prevent these conditions.

A second pharmaceutical approach is to administer promotility agents that act to increase LES tone and, in some instances, improve esophageal acid clearance and accelerate gastric emptying. Bethanechol, a cholinergic agonist that enhances LES tone, was frequently used in the past. It is no longer widely employed, however, because of its poor efficacy, a high incidence of side effects, and a tendency to stimulate gastric acid secretion.

Esophageal strictures can be treated by forcible dilatation using flexible tapered bougies that are swallowed by the patient. Dilatation also can be performed by endoscopically using balloons. Although such dilatation is usually effective, strictures frequently recur if gastroesophageal reflux is not controlled.

The lower esophageal acid exclusion barrier can be restored by a surgical procedure in which the distal portion of esophagus is anchored in the abdomen by wrapping part of the fundus of the stomach around it. This procedure, called fundoplication, is intended to reestablish the normal anatomic relationships and reinforce the LES. Although fundoplication typically eliminates gastroesophageal reflux and affords complete resolution of symptoms, this procedure is extremely invasive, and often causes unwelcome side effects. After fundoplication surgery, for example, some patients are unable to belch and complain of frequent abdominal distention, a phenomenon known as gas-bloat syndrome. In addition, some patients who have good relief initially will develop recurrent reflux after a period of years.

SUMMARY OF THE INVENTION

The present invention provides systems, methods and apparatus for applying high frequency electrical energy to treat tissue in regions of the digestive system. The present invention is particularly suited for applying electrical energy to the lower esophageal sphincter to treat gastroesophageal reflux.

In one aspect of the invention, a method of the present invention comprises positioning an electrosurgical instrument adjacent a tissue structure of the lower sphincter so that one or more electrode terminal(s) are brought into at least partial contact or close proximity with the body structure. High frequency voltage is applied between the electrode terminal(s) and one or more return electrode(s) to elevate the temperature of collagen fibers within the tissue of the lower sphincter from body temperature (about 37° C.) to a tissue temperature in the range of about 45° C. to 90° C., usually about 60° C. to 70° C. This temperature elevation substantially irreversibly contracts the collagen fibers within the tissue to tighten the lower sphincter and prevent or greatly reduce gastroesophageal reflux. The electrosurgical instrument may comprise a catheter that is advanced transluminally or through the patient's mouth and esophagus down to the lower sphincter, or a more rigid probe that is introduced through a percutaneous or open penetration in the patient.

In a preferred embodiment, an electrically conducting fluid is provided between the electrode terminal(s) and one or more return electrode(s) positioned proximal to the electrode terminal(s) to provide a current flow path from the electrode terminal(s) away from the tissue to the return electrode(s). The current flow path may be generated by directing an electrically conducting fluid along a fluid path past the return electrode and to the target site, or by locating a viscous electrically conducting fluid, such as a gel, at the target site, and submersing the electrode terminal(s) and the return electrode(s) within the conductive gel. The collagen fibers may be heated either by passing the electric current through the tissue to a selected depth before the current returns to the return electrode(s) and/or by heating the electrically conducting fluid and generating a jet or plume of heated fluid, which is directed towards the target tissue. In the latter embodiment, the electric current may not pass into the tissue at all. In both embodiments, the heated fluid and/or the electric current elevates the temperature of the collagen sufficiently to cause hydrothermal shrinkage of the collagen fibers.

In another aspect of the invention, a sufficient high frequency voltage is applied between the electrode terminal (s) and one or more return electrode(s) to volumetrically remove at least a portion of the lower sphincter. Specifically, high frequency voltage is applied between the electrode terminal(s) and one or more return electrode(s) to remove a small tissue segment, channel or hole from the region near or in the lower sphincter to shrink the sphincter and prevent swelling, due to the formation of scar tissue as the wound heals. The high frequency voltage may be selected to effect a small amount of thermal damage to the walls of the channel or hole to facilitate the formation of scar tissue without extending this thermal damage beyond the immediate region of the target site The electrode terminal(s) may be translated relative to the lower sphincter during or after the application of electrical energy to sculpt a void within the lower sphincter, such as a hole, channel, stripe, crater, or the like. In some embodiments, the electrode terminal(s) are axially translated toward the lower sphincter to bore one or more channel(s) or hole(s) through a portion of the structure. In other embodiments, the electrode terminal(s) are translated across the lower sphincter to form one or more stripe(s) or channel(s). In most embodiments, electrically conducting fluid, such as isotonic saline, is located between the electrode terminal(s) and the tissue. In the bipolar modality, the conducting fluid generates a current flow path between the electrode terminal(s) and one or more return electrode(s). High frequency voltage is then applied between the electrode terminal(s) and the return electrode(s) through the current flow path created by the electrically conducting fluid.

In a specific configuration, the tissue is removed by molecular dissociation or disintegration processes. In these embodiments, the high frequency voltage applied to the electrode terminal(s) is sufficient to vaporize an electrically conductive fluid (e.g., gel or saline) between the electrode terminal(s) and the tissue. Within the vaporized fluid, a ionized plasma is formed and charged particles (e.g., electrons) are accelerated towards the tissue to cause the molecular breakdown or disintegration of several cell layers of the tissue. This molecular dissociation is accompanied by the volumetric removal of the tissue. The short range of the accelerated charged particles within the tissue confines the molecular dissociation process to the tissue surface layer to minimize damage and necrosis to the underlying tissue. This process can be precisely controlled to effect the volumetric removal of tissue as thin as 10 to 150 microns with minimal heating of, or damage to, surrounding or underlying tissue structures. A more complete description of this phenomena is described in commonly assigned U.S. Pat. No. 5,683,366, previously incorporated herein by reference.

Apparatus according to the present invention generally include an electrosurgical probe or catheter having a shaft with proximal and distal ends, one or more electrode terminal(s) at the distal end and one or more connectors coupling the electrode terminal(s) to a high frequency power supply. The apparatus will further include one or more return electrode(s) either located on an outer surface of the patient, or on the probe shaft or another instrument. The high frequency power supply is configured to apply a voltage difference between electrode terminal(s) and the return electrode(s) that is sufficient to effect contraction of collagen fibers within the tissue structure to stiffen the lower sphincter.

The apparatus will preferably further include a fluid delivery element for delivering electrically conducting fluid to the electrode terminal(s) and the target site. The fluid delivery element may be located on the instrument, e.g., a fluid lumen or tube, or it may be part of a separate instrument. Alternatively, an electrically conducting gel or spray, such as a saline electrolyte or other conductive gel, may be applied the target site. In this embodiment, the apparatus may not have a fluid delivery element. In both embodiments, the electrically conducting fluid will preferably generate a current flow path between the electrode terminal(s) and one or more return electrode(s). In an exemplary embodiment, the return electrode is located on the instrument and spaced a sufficient distance from the electrode terminal(s) to substantially avoid or minimize current shorting therebetween and to shield the return electrode from tissue at the target site.

In a specific configuration, the electrosurgical instrument comprises a catheter designed for advancement through the patient's mouth, down the esophagus into the region of the lower sphincter. In this embodiment, the catheter may optionally include an endoscope, or the system may include a separate endoscope. The catheter shaft will include an electrically insulating electrode support member having a tissue treatment surface at the distal end of the shaft. One or more electrode terminal(s) are coupled to, or integral with, the electrode support member such that the electrode terminal(s) are spaced from the return electrode. In one embodiment, the catheter includes an electrode array having a plurality of electrically isolated electrode terminals embedded into the electrode support member such that the electrode terminals extend about 0.0 mm to about 10 mm. In this embodiment, the catheter will further include one or more lumens for delivering electrically conductive fluid to one or more openings around the tissue treatment surface of the electrode support member. In an exemplary embodiment, the lumen will extend through a fluid tube exterior to the catheter shaft that ends proximal to the return electrode.

The system may optionally include a temperature controller coupled to one or more temperature sensors at or near the distal end of the instrument. The controller adjusts the output voltage of the power supply in response to a temperature set point and the measured temperature value. The temperature sensor may be, for example, a thermocouple, located in the insulating support that measures a temperature at the distal end of the instrument. In this embodiment, the temperature set point will preferably be one that corresponds to a surface temperature of tissue that results in the contraction of the collagen within the underlying tissue, i.e., about 60° C. to 70° C. Alternatively, the temperature sensor may directly measure the tissue temperature (e.g., infrared sensor). This embodiment is advantageous in situations when the surgeon is moving the instrument transversely across the tissue.

DESCRIPTION OF SPECIFIC EMBODIMENTS

Figure 1:
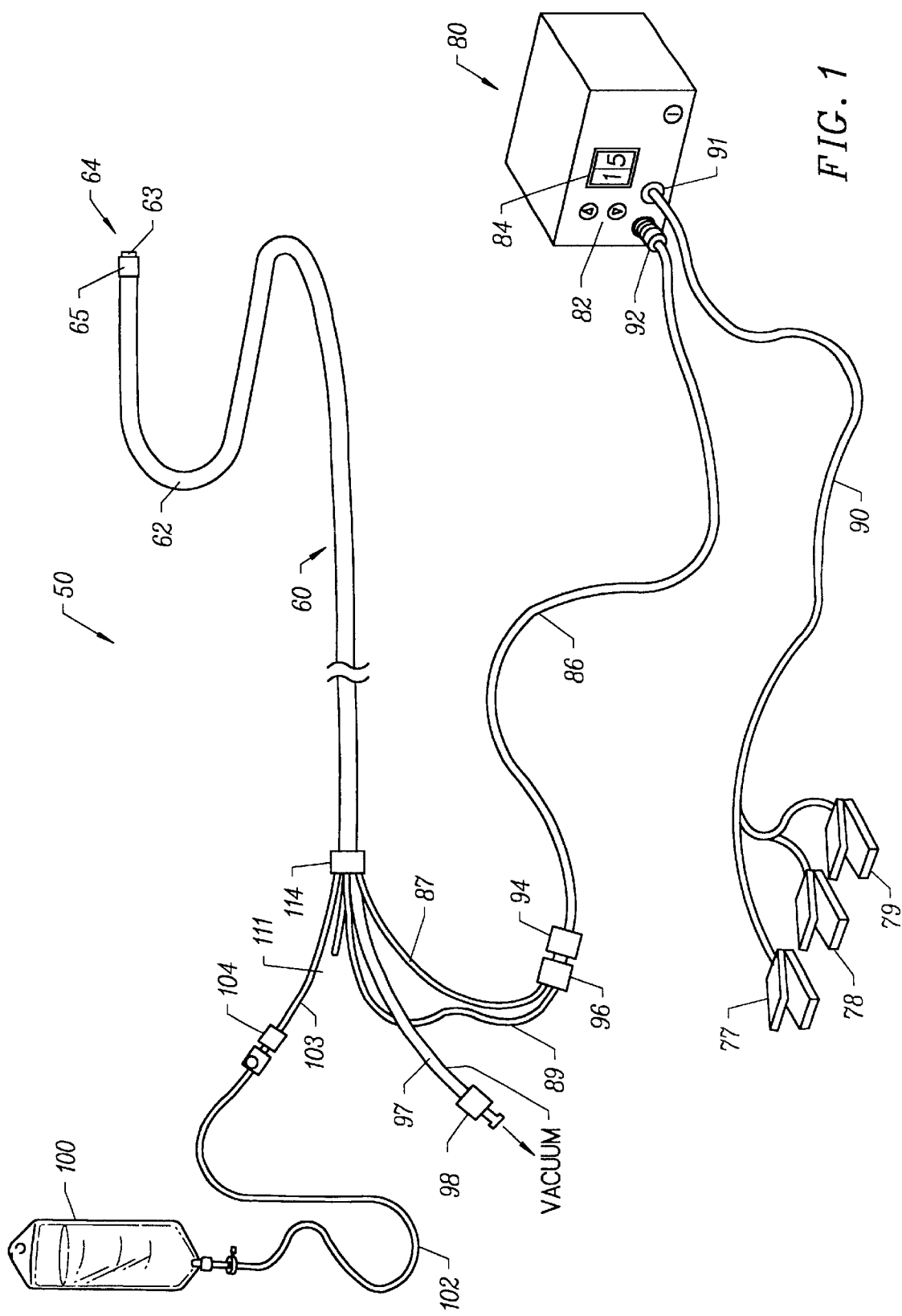
FIG. 1 illustrates a catheter system for electrosurgical treatment of body structures within the gastrointestinal tract according to the present invention.

The present invention provides systems and methods for selectively applying electrical energy to a target location within or on a patient's body, particularly including tissue in the digestive system, such as the pharynx, esophagus, stomach, intestines, liver, pancreas and rectum. These procedures may be performed through the mouth and throat using speculae or gags, or using endoscopic techniques (e.g., laparascopy). These procedures may include the removal of polyps, lesions, carcinomas, adenocarcinomas (e.g., Barrett's esophagus), tumors, lymphomas, leiomyomas, and other gastrointestinal neoplasms, such as those neoplasms occurring in the hollow organs of the gastrointestinal tract, tumors that develop in the extra hepatic biliary system or in the head of the pancreas (e.g., invasive malignant tumors such as lymphoma and carcinoma or benign tumors), tracheal stenosis and vocal cord or esophageal polyps and lesions.

For convenience, the remaining disclosure will be directed specifically to the treatment of gastroesophageal reflux, but it will be appreciated that the system and method can be applied equally well to procedures involving other tissues of the body, as well as to other procedures including open procedures, intravascular procedures, urology, laparascopy, arthroscopy, thoracotomy or other cardiac procedures, cosmetic surgery, orthopedics, gynecology, otorhinolaryngology, spinal and neurologic procedures, oncology and the like.

In the present invention, high frequency (RF) electrical energy is applied to one or more electrode terminals in the presence of electrically conductive fluid to remove and/or modify the structure of tissue structures. Depending on the specific procedure, the present invention may be used to: (1) volumetrically remove tissue, bone or cartilage (i.e., ablate or effect molecular dissociation of the tissue structure; (2) cut or resect tissue; (3) shrink or contract collagen connective tissue; and/or (4) coagulate severed blood vessels.

In some procedures, the tissue structures are volumetrically removed or ablated by applying a high frequency voltage difference between one or more electrode terminal (s) and one or more return electrode(s). The voltage difference is sufficient to develop high electric field intensities in the vicinity of the target tissue site, which lead to electric field induced molecular breakdown of target tissue through molecular dissociation (rather than thermal evaporation or carbonization). The tissue structure is volumetrically removed through molecular disintegration of larger organic molecules into smaller molecules and/or atoms, such as hydrogen, oxygen, nitrogen, oxides of carbon, hydrocarbons and nitrogen compounds. This molecular disintegration completely removes the tissue structure, as opposed to dehydrating the tissue material by the removal of liquid within the cells of the tissue, as is typically the case with electrosurgical desiccation and vaporization.

The high electric field intensities may be generated by applying a high frequency voltage that is sufficient to vaporize an electrically conducting fluid over at least a portion of the electrode terminal(s) in the region between the distal tip of the electrode terminal(s) and the target tissue. The electrically conductive fluid may be a gas or liquid, such as isotonic saline, delivered to the target site, or a viscous fluid, such as a gel, that is located at the target site. In the latter embodiment, the electrode terminal(s) are submersed in the electrically conductive gel during the surgical procedure. Since the vapor layer or vaporized region has a relatively high electrical impedance, it increases the voltage differential between the electrode terminal tip and the tissue and causes ionization within the vapor layer due to the presence of an ionizable species (e.g., sodium when isotonic saline is the electrically conducting fluid). This ionization, under optimal conditions, induces the discharge of energetic electrons and photons from the vapor layer and to the surface of the target tissue. This energy may be in the form of energetic photons (e.g., ultraviolet radiation), energetic particles (e.g., electrons) or a combination thereof. A more detailed description of this cold ablation phenomena, termed Coblation™, can be found in commonly assigned U.S. Pat. No. 5,683,366 the complete disclosure of which is incorporated herein by reference.

The present invention applies high frequency (RF) electrical energy in an electrically conducting fluid environment to remove (i.e., resect, cut or ablate) or contract a tissue structure, and to seal transected vessels within the region of the target tissue. The present invention is particularly useful for sealing larger arterial vessels, e.g., on the order of 1 mm or greater. In some embodiments, a high frequency power supply is provided having an ablation mode, wherein a first voltage is applied to an electrode terminal sufficient to effect molecular dissociation or disintegration of the tissue, and a coagulation mode, wherein a second, lower voltage is applied to an electrode terminal (either the same or a different electrode) sufficient to achieve hemostasis of severed vessels within the tissue. In other embodiments, an electrosurgical instrument is provided having one or more coagulation electrode(s) configured for sealing a severed vessel, such as an arterial vessel, and one or more electrode terminals configured for either contracting the collagen fibers within the tissue or removing (ablating) the tissue, e.g., by applying sufficient energy to the tissue to effect molecular dissociation. In the latter embodiments, the coagulation electrode(s) may be configured such that a single voltage can be applied to coagulate with the coagulation electrode(s), and to ablate or contract with the electrode terminal(s). In other embodiments, the power supply is combined with the coagulation instrument such that the coagulation electrode is used when the power supply is in the coagulation mode (low voltage), and the electrode terminal(s) are used when the power supply is in the ablation mode (higher voltage).

In the method of the present invention, one or more electrode terminals are brought into close proximity to tissue at a target site, and the power supply is activated in the ablation mode such that sufficient voltage is applied between the electrode terminals and the return electrode to volumetrically remove the tissue through molecular dissociation, as described below. During this process, vessels within the tissue will be severed. Smaller vessels will be automatically sealed with the system and method of the present invention. Larger vessels, and those with a higher flow rate, such as arterial vessels, may not be automatically sealed in the ablation mode. In these cases, the severed vessels may be sealed by activating a control (e.g., a foot pedal) to reduce the voltage of the power supply into the coagulation mode. In this mode, the electrode terminals may be pressed against the severed vessel to provide sealing and/or coagulation of the vessel. Alternatively, a coagulation electrode located on the same or a different instrument may be pressed against the severed vessel. Once the vessel is adequately sealed, the surgeon activates a control (e.g., another foot pedal) to increase the voltage of the power supply back into the ablation mode.

The present invention is particularly useful for removing or ablating tissue around nerves, such as spinal, cranial nerves or peripheral nerves. One of the significant drawbacks with the prior art microdebriders and lasers is that these devices do not differentiate between the target tissue and the surrounding nerves or bone. Therefore, the surgeon must be extremely careful during these procedures to avoid damage to the bone or nerves within and around the gastrointestinal tract. In the present invention, the Coblation™ process for removing tissue results in extremely small depths of collateral tissue damage as discussed above. This allows the surgeon to remove tissue close to a nerve without causing collateral damage to the nerve fibers.

In addition to the generally precise nature of the novel mechanisms of the present invention, applicant has discovered an additional method of ensuring that adjacent nerves are not damaged during tissue removal. According to the present invention, systems and methods are provided for distinguishing between the fatty tissue immediately surrounding nerve fibers and the normal tissue that is to be removed during the procedure. Nerves usually comprise a connective tissue sheath, or endoneurium, enclosing the bundles of nerve fibers to protect these nerve fibers. This protective tissue sheath typically comprises a fatty tissue (e.g., adipose tissue) having substantially different electrical properties and higher molecular body energies than the normal target tissue. The system of the present invention measures both the electrical properties of the tissue at the tip of the instrument with one or more electrode terminal(s) and delivers energetic particles which preferentially disintegrate non-fatty tissue. These electrical properties may include electrical conductivity at one, several or a range of frequencies (e.g., in the range from 1 kHz to 100 MHz), dielectric constant, capacitance or combinations of these. In this embodiment, an audible signal may be produced when the sensing electrode(s) at the tip of the instrument detects the fatty tissue surrounding a nerve, or direct feedback control can be provided to only supply power to the electrode terminal(s) either individually or to the complete array of electrodes, if and when the tissue encountered at the tip or working end of the instrument is normal tissue based on the measured electrical properties.

In one embodiment, the current limiting elements (discussed in detail above) are configured such that the electrode terminals will shut down or turn off when the electrical impedance reaches a threshold level. When this threshold level is set to the impedance of the fatty tissue surrounding nerves, the electrode terminals will shut off whenever they come in contact with, or in close proximity to, nerves. Meanwhile, the other electrode terminals, which are in contact with or in close proximity to tissue, will continue to conduct electric current to the return electrode. This selective ablation or removal of lower impedance tissue in combination with the Coblation™ mechanism of the present invention allows the surgeon to precisely remove tissue around nerves or bone.

In addition to the above, applicant has discovered that the Coblation™ mechanism of the present invention can be manipulated to ablate or remove certain tissue structures, while having little effect on other tissue structures. As discussed above, the present invention uses a technique of vaporizing electrically conductive fluid to form a plasma layer or pocket around the electrode terminal(s), and then inducing the discharge of energy from this plasma or vapor layer to break the molecular bonds of the tissue structure. Based on initial experiments, applicants believe that the free electrons within the ionized vapor layer are accelerated in the high electric fields near the electrode tip(s). When the density of the vapor layer (or within a bubble formed in the electrically conducting liquid) becomes sufficiently low (i.e., less than approximately $10^{20}$ atoms/cm$^3$ for aqueous solutions), the electron mean free path increases to enable subsequently injected electrons to cause impact ionization within these regions of low density (i.e., vapor layers or bubbles). Energy evolved by the energetic electrons (e.g., 4 to 5 eV) can subsequently bombard a molecule and break its bonds, dissociating a molecule into free radicals, which then combine into final gaseous or liquid species.

The energy evolved by the energetic electrons may be varied by adjusting a variety of factors, such as: the number of electrode terminals; electrode size and spacing; electrode surface area; asperities and sharp edges on the electrode surfaces; electrode materials; applied voltage and power; current limiting means, such as inductors; electrical conductivity of the fluid in contact with the electrodes; density of the fluid; and other factors. Accordingly, these factors can be manipulated to control the energy level of the excited electrons. Since different tissue structures have different molecular bonds, the present invention can be configured to break the molecular bonds of certain tissue, while having too low an energy to break the molecular bonds of other tissue. For example, fatty tissue, (e.g., adipose) tissue has double bonds that require a substantially higher energy level than 4 to 5 eV to break. Accordingly, the present invention in its current configuration generally does not ablate or remove such fatty tissue. Of course, factors may be changed such that these double bonds can be broken (e.g., increasing voltage or changing the electrode configuration to increase the current density at the electrode tips).

In other procedures, e.g., lower esophageal sphincter stiffening, it is desired to shrink or contract collagen connective tissue at the target site. In these procedures, the RF energy heats the tissue directly by virtue of the electrical current flow therethrough, and/or indirectly through the exposure of the tissue to fluid heated by RF energy, to elevate the tissue temperature from normal body temperatures (e.g., 37° C.) to temperatures in the range of 45° C. to 90° C., preferably in the range from about 60° C. to 70° C. Thermal shrinkage of collagen fibers occurs within a small temperature range which, for mammalian collagen is in the range from 60° C. to 70° C. (Deak, G., et al., "The Thermal Shrinkage Process of Collagen Fibres as Revealed by Polarization Optical Analysis of Topooptical Staining Reactions," Acta Morphologica Acad. Sci. of Hungary, Vol. 15(2), pp 195–208, 1967). Collagen fibers typically undergo thermal shrinkage in the range of 60° C. to about 70° C. Previously reported research has attributed thermal shrinkage of collagen to the cleaving of the internal stabilizing cross-linkages within the collagen matrix (Deak, ibid). It has also been reported that when the collagen temperature is increased above 70° C., the collagen matrix begins to relax again and the shrinkage effect is reversed resulting in no net shrinkage (Allain, J. C., et al., "Isometric Tensions Developed During the Hydrothermal Swelling of Rat Skin," Connective Tissue Research, Vol. 7, pp 127–133, 1980). Consequently, the controlled heating of tissue to a precise depth is critical to the achievement of therapeutic collagen shrinkage. A more detailed description of collagen shrinkage can be found in U.S. patent application Ser. No. 08/942,580, filed on Oct. 2, 1997.

The preferred depth of heating to effect the shrinkage of collagen in the heated region (i.e., the depth to which the tissue is elevated to temperatures between 60° C. to 70° C.) generally depends on (1) the thickness of the tissue, (2) the location of nearby structures (e.g., nerves) that should not be exposed to damaging temperatures, and/or (3) the location of the collagen tissue layer within which therapeutic shrinkage is to be effected. The depth of heating is usually in the range from 0 to 3.5 mm. In the case of collagen within the LES, the depth of heating is preferably in the range from about 0.5 to about 3.5 mm.

The electrosurgical instrument (e.g., probe or catheter) will comprise a shaft having a proximal end and a distal end which supports one or more electrode terminal(s). The shaft may assume a wide variety of configurations, with the primary purpose being to mechanically support the active electrode and permit the treating physician to manipulate the electrode from a proximal end of the shaft. The shaft may be rigid or flexible, with flexible shafts optionally being combined with a generally rigid external tube for mechanical support. Flexible shafts may be combined with pull wires, shape memory actuators, and other known mechanisms for effecting selective deflection of the distal end of the shaft to facilitate positioning of the electrode array. The shaft will usually include a plurality of wires or other conductive elements running axially therethrough to permit connection of the electrode array to a connector at the proximal end of the shaft.

For procedures within the esophagus, the shaft will have a suitable diameter and length to allow the surgeon to reach the target site (e.g., lower sphincter) by delivering a catheter shaft through the mouth and esophagus or a probe shaft through another opening (e.g., a surgically created opening during the procedure). In the former procedures, the catheter shaft will usually have a length in the range of about 20–50 cm, and a diameter in the range of about 0.5 to 15 mm. In the latter procedures, the probe shaft will usually have a length in the range of about 5–25 cm, and a diameter in the range of about 0.5 to 15 mm. For procedures requiring the formation of a small hole or channel in tissue, the shaft diameter will usually be less than 3 mm, preferably less than about 1 mm. For procedures that require advancement through the mouth and upper throat, the shaft will have any suitable length and diameter that would facilitate handling by the surgeon, and it will be suitably designed to access the target site. For example, the shaft may be flexible, or have a distal bend to accommodate the bend in the patient's throat. In this regard, the shaft may be a rigid shaft having a specifically designed bend to correspond with the geometry of the mouth and throat, or it may have a flexible distal end, or it may be part of a catheter. In any of these embodiments, the shaft may also be introduced through rigid or flexible endoscopes. Specific shaft designs will be described in detail in connection with the figures hereinafter.

The current flow path between the electrode terminal(s) and the return electrode(s) may be generated by submerging the tissue site in an electrical conducting fluid (e.g., within a viscous fluid, such as an electrically conductive gel) or by directing an electrically conducting fluid along a fluid path to the target site (i.e., a liquid, such as isotonic saline, or a gas, such as argon). This latter method is particularly effective in a dry environment (i.e., the tissue is not submerged in fluid) because the electrically conducting fluid provides a suitable current flow path from the electrode terminal to the return electrode. A more complete description of an exemplary method of directing electrically conducting fluid between the active and return electrodes is described in U.S. Pat. No. 5,697,800, previously incorporated herein by reference.

In some procedures, it may also be necessary to retrieve or aspirate the electrically conductive fluid after it has been directed to the target site. For example, in procedures in the mouth, throat or esophagus, it may be desirable to aspirate the fluid so that it does not flow down the patient's throat. In addition, it may be desirable to aspirate small pieces of tissue that are not completely disintegrated by the high frequency energy, or other fluids at the target site, such as blood, mucus, the gaseous products of ablation, etc. Accordingly, the system of the present invention will usually include a suction lumen in the instrument, or on another instrument, for aspirating fluids from the target site.

The present invention may use a single active electrode terminal or an electrode array distributed over a contact surface of a instrument. In the latter embodiment, the electrode array usually includes a plurality of independently current-limited and/or power-controlled electrode terminals to apply electrical energy selectively to the target tissue while limiting the unwanted application of electrical energy to the surrounding tissue and environment resulting from power dissipation into surrounding electrically conductive liquids, such as blood, normal saline, electrically conductive gel and the like. The electrode terminals may be independently current-limited by isolating the terminals from each other and connecting each terminal to a separate power source that is isolated from the other electrode terminals. Alternatively, the electrode terminals may be connected to each other at either the proximal or distal ends of the instrument to form a single wire that couples to a power source.

In one configuration, each individual electrode terminal in the electrode array is electrically insulated from all other electrode terminals in the array within said instrument and is connected to a power source which is isolated from each of the other electrode terminals in the array or to circuitry which limits or interrupts current flow to the electrode terminal when low resistivity material (e.g., blood, electrically conductive saline irrigant or electrically conductive gel) causes a lower impedance path between the return electrode and the individual electrode terminal. The isolated power sources for each individual electrode terminal may be separate power supply circuits having internal impedance characteristics which limit power to the associated electrode terminal when a low impedance return path is encountered. By way of example, the isolated power source may be a user selectable constant current source. In this embodiment, lower impedance paths will automatically result in lower resistive heating levels since the heating is proportional to the square of the operating current times the impedance. Alternatively, a single power source may be connected to each of the electrode terminals through independently actuatable switches, or by independent current limiting elements, such as inductors, capacitors, resistors and/or combinations thereof. The current limiting elements may be provided in the instrument, connectors, cable, controller or along the conductive path from the controller to the distal tip of the instrument. Alternatively, the resistance and/or capacitance may occur on the surface of the active electrode terminal(s) due to oxide layers which form selected electrode terminals (e.g., titanium or a resistive coating on the surface of metal, such as platinum).

The tip region of the instrument may comprise many independent electrode terminals designed to deliver electrical energy in the vicinity of the tip. The selective application of electrical energy to the conductive fluid is achieved by connecting each individual electrode terminal and the return electrode to a power source having independently controlled or current limited channels. The return electrode(s) may comprise a single tubular member of conductive material proximal to the electrode array at the tip which also serves as a conduit for the supply of the electrically conducting fluid between the active and return electrodes. Alternatively, the instrument may comprise an array of return electrodes at the distal tip of the instrument (together with the active electrodes) to maintain the electric current at the tip. The application of high frequency voltage between the return electrode(s) and the electrode array results in the generation of high electric field intensities at the distal tips of the electrode terminals with conduction of high frequency current from each individual electrode terminal to the return electrode. The current flow from each individual electrode terminal to the return electrode(s) is controlled by either active or passive means, or a combination thereof, to deliver electrical energy to the surrounding conductive fluid while minimizing energy delivery to surrounding (non-target) tissue.

The application of a high frequency voltage between the return electrode(s) and the electrode terminal(s) for appropriate time intervals effects cutting, removing, ablating, shaping, contracting or otherwise modifying the target tissue. The tissue volume over which energy is dissipated (i.e., a high current density exists) may be precisely controlled, for example, by the use of a multiplicity of small electrode terminals whose effective diameters or principal dimensions range from about 5 mm to 0.01 mm, preferably from about 2 mm to 0.05 mm, and more preferably from about 1 mm to 0.1 mm. Electrode areas for both circular and non-circular terminals will have a contact area (per electrode terminal) below 25 mm$^2$, preferably being in the range from 0.0001 mm$^2$ to 1 mm$^2$, and more preferably from 0.005 mm$^2$ to 0.5 mm$^2$. The circumscribed area of the electrode array is in the range from 0.25 mm$^2$ to 75 mm$^2$, preferably from 0.5 mm$^2$ to 40 mm$^2$, and will usually include at least one electrode terminal, often at least two isolated electrode terminals, preferably at least five electrode terminals, often greater than 10 electrode terminals and even 50 or more electrode terminals, disposed over the distal contact surfaces on the shaft. The use of small diameter electrode terminals increases the electric field intensity and reduces the extent or depth of tissue heating as a consequence of the divergence of current flux lines which emanate from the exposed surface of each electrode terminal. These electrode terminals will typically have an extension length in the range of about 0.0 to 3.0 mm.

The area of the tissue treatment surface can vary widely, and the tissue treatment surface can assume a variety of geometries, with particular areas and geometries being selected for specific applications. Active electrode surfaces can have areas in the range from 0.25 mm$^2$ to 75 mm$^2$, usually being from about 0.5 mm$^2$ to 40 mm$^2$. The geometries can be planar, concave, convex, hemispherical, conical, linear "in-line" array or virtually any other regular or irregular shape. Most commonly, the active electrode(s) or electrode terminal(s) will be formed at the distal tip of the electrosurgical instrument shaft, frequently being planar, disk-shaped, or hemispherical surfaces for use in reshaping procedures or being linear arrays for use in cutting. Alternatively or additionally, the active electrode(s) may be formed on lateral surfaces of the electrosurgical instrument shaft (e.g., in the manner of a spatula), facilitating access to certain body structures in endoscopic procedures.

The electrically conducting fluid should have a threshold conductivity to provide a suitable conductive path between the return electrode(s) and the electrode terminal(s). The electrical conductivity of the fluid (in units of milliSiemans per centimeter or mS/cm) will usually be greater than 0.2 mS/cm, preferably will be greater than 2 mS/cm and more preferably greater than 10 mS/cm. In an exemplary embodiment, the electrically conductive fluid is isotonic saline, which has a conductivity of about 17 mS/cm.

In some embodiments, the electrode support and the fluid outlet may be recessed from an outer surface of the instrument or handpiece to confine the electrically conductive fluid to the region immediately surrounding the electrode support. In addition, the shaft may be shaped so as to form a cavity around the electrode support and the fluid outlet. This helps to assure that the electrically conductive fluid will remain in contact with the electrode terminal(s) and the return electrode(s) to maintain the conductive path therebetween. In addition, this will help to maintain a vapor or plasma layer between the electrode terminal(s) and the tissue at the treatment site throughout the procedure, which reduces the thermal damage that might otherwise occur if the vapor layer were extinguished due to a lack of conductive fluid. Provision of the electrically conductive fluid around the target site also helps to maintain the tissue temperature at desired levels.

The voltage applied between the return electrode(s) and the electrode array will be at high or radio frequency, typically between about 5 kHz and 20 MHz, usually being between about 30 kHz and 2.5 MHz, preferably being between about 50 kHz and 500 kHz, more preferably less than 350 kHz, and most preferably between about 100 kHz and 200 kHz. The RMS (root mean square) voltage applied will usually be in the range from about 5 volts to 1000 volts, preferably being in the range from about 10 volts to 500 volts depending on the electrode terminal size, the operating frequency and the operation mode of the particular procedure or desired effect on the tissue (i.e., contraction, coagulation or ablation). Typically, the peak-to-peak voltage will be in the range of 10 to 2000 volts, preferably in the range of 20 to 1200 volts and more preferably in the range of about 40 to 800 volts (again, depending on the electrode size, the operating frequency and the operation mode).

As discussed above, the voltage is usually delivered in a series of voltage pulses or alternating current of time varying voltage amplitude with a sufficiently high frequency (e.g., on the order of 5 kHz to 20 MHz) such that the voltage is effectively applied continuously (as compared with e.g., lasers claiming small depths of necrosis, which are generally pulsed about 10 to 20 Hz). In addition, the duty cycle (i.e., cumulative time in any one-second interval that energy is applied) is on the order of about 50% for the present invention, as compared with pulsed lasers which typically have a duty cycle of about 0.0001%.

The preferred power source of the present invention delivers a high frequency current selectable to generate average power levels ranging from several milliwatts to tens of watts per electrode, depending on the volume of target tissue being heated, and/or the maximum allowed temperature selected for the instrument tip. The power source allows the user to select the voltage level according to the specific requirements of a particular otorhinolaryngology procedure, arthroscopic surgery, dermatological procedure, ophthalmic procedures, open surgery or other endoscopic surgery procedure. A description of a suitable power source can be found in Provisional Application No. 60/075,059 filed Feb. 18, 1998, previously incorporated herein by reference.

The power source may be current limited or otherwise controlled so that undesired heating of the target tissue or surrounding (non-target) tissue does not occur. In a presently preferred embodiment of the present invention, current limiting inductors are placed in series with each independent electrode terminal, where the inductance of the inductor is in the range of 10 uH to 50,000 uH, depending on the electrical properties of the target tissue, the desired tissue heating rate and the operating frequency. Alternatively, capacitor-inductor (LC) circuit structures may be employed, as described previously in co-pending PCT application No. PCT/US94/05168, the complete disclosure of which is incorporated herein by reference. Additionally, current limiting resistors may be selected. Preferably, these resistors will have a large positive temperature coefficient of resistance so that, as the current level begins to rise for any individual electrode terminal in contact with a low resistance medium (e.g., saline irrigant or conductive gel), the resistance of the current limiting resistor increases significantly, thereby minimizing the power delivery from said electrode terminal into the low resistance medium (e.g., saline irrigant or conductive gel).

It should be clearly understood that the invention is not limited to electrically isolated electrode terminals, or even to a plurality of electrode terminals. For example, the array of active electrode terminals may be connected to a single lead that extends through the instrument shaft to a power source of high frequency current. Alternatively, the instrument may incorporate a single electrode that extends directly through the instrument shaft or is connected to a single lead that extends to the power source. The active electrode may have a ball shape (e.g., for tissue vaporization and desiccation), a twizzle shape (for vaporization and needle-like cutting), a spring shape (for rapid tissue debulking and desiccation), a twisted metal shape, an annular or solid tube shape or the like. Alternatively, the electrode may comprise a plurality of filaments, a rigid or flexible brush electrode (for debulking a tumor, such as a fibroid, bladder tumor or a prostate adenoma), a side-effect brush electrode on a lateral surface of the shaft, a coiled electrode or the like. In one embodiment, the instrument comprises a single active electrode terminal that extends from an atraumatic insulating member, e.g. at the distal end of the instrument. The active electrode member tapers toward its distal end, and may form a sharp point at the distal end. The atraumatic insulating member may be movable relative to the active electrode so that the insulating member can be advanced and retracted to shield and/or expose the active electrode from the surrounding tissue.

Referring now to FIG. 1, a catheter system 50 for treating the digestive system is illustrated according to the present invention. Catheter system 50 generally comprises an electrosurgical catheter 60 connected to a power supply 80 by an interconnecting cable 86 for providing high frequency voltage to a target tissue and an irrigant reservoir or source 100 for providing electrically conducting fluid to the target site. Catheter 60 generally comprises an elongate, flexible shaft body 62 including a working end 64 at the distal end of body 62. The proximal portion of catheter 60 includes a multi-lumen fitment 114 which provides for interconnections between lumens and electrical leads within catheter 60 and conduits and cables proximal to fitment 114. By way of example, a catheter electrical connector 96 is removably connected to a distal cable connector 94 which, in turn, is removably connectable to generator 80 through connector 92. One or more electrically conducting lead wires (not shown) within catheter 60 extend between one or more active electrodes 63 at working end 64 and one or more corresponding electrical terminals (also not shown) in catheter connector 96 via active electrode cable branch 87. Similarly, one or more return electrodes 65 at the working end 64 of catheter body 62 are coupled to a return electrode cable branch 89 of catheter connector 96 by lead wires (not shown). Of course, a single cable branch (not shown) may be used for both active and return electrodes.

Power supply 80 has an operator controllable voltage level adjustment 82 to change the applied voltage level, which is observable at a voltage level display 84. Power supply 80 also includes first, second and third foot pedals 77, 78, 79 and a cable 90 which is removably coupled to power supply 80. The foot pedals 77, 78, 79 allow the surgeon to remotely adjust the energy level applied to electrode terminals 63. In an exemplary embodiment, first foot pedal 77 is used to place the power supply into the "ablation" mode and second foot pedal 78 places power supply 80 into a "subablation" mode (i.e., contraction, coagulation or other types of tissue modification without volumetric tissue removal). The third foot pedal 79 allows the user to adjust the voltage level within the "ablation" mode. In the ablation mode, a sufficient voltage is applied to the electrode terminals to establish the requisite conditions for molecular dissociation of the tissue (i.e., vaporizing a portion of the electrically conductive fluid, ionizing charged particles within the vapor layer and accelerating these charged particles against the tissue). As discussed above, the requisite voltage level for ablation will vary depending on the number, size, shape and spacing of the electrodes, the distance in which the electrodes extend from the support member, etc. Once the surgeon places the power supply in the "ablation" mode, voltage level adjustment 82 or third foot pedal 79 may be used to adjust the voltage level to adjust the degree or aggressiveness of the ablation.

Of course, it will be recognized that the voltage and modality of the power supply may be controlled by other input devices. However, applicant has found that foot pedals are convenient methods of controlling the power supply while manipulating the instrument during a surgical procedure.

In the subablation mode, the power supply 80 applies a low enough voltage to the electrode terminals to avoid vaporization of the electrically conductive fluid and subsequent molecular dissociation of the tissue. The surgeon may automatically toggle the power supply between the ablation and subablation modes by alternatively stepping on foot pedals 77, 78, respectively. This allows, for example, the surgeon to quickly move between coagulation and ablation in situ, without having to remove his/her concentration from the surgical field or without having to request an assistant to switch the power supply. By way of example, as the surgeon is sculpting soft tissue in the ablation mode, the instrument typically will simultaneously seal and/or coagulation small severed vessels within the tissue. However, larger vessels, or vessels with high fluid pressures (e.g., arterial vessels) may not be sealed in the ablation mode. Accordingly, the surgeon can simply step on foot pedal 78, automatically lowering the voltage level below the threshold level for ablation, and apply sufficient pressure onto the severed vessel for a sufficient period of time to seal and/or coagulate the vessel. After this is completed, the surgeon may quickly move back into the ablation mode by stepping on foot pedal 77.

Figure 2:
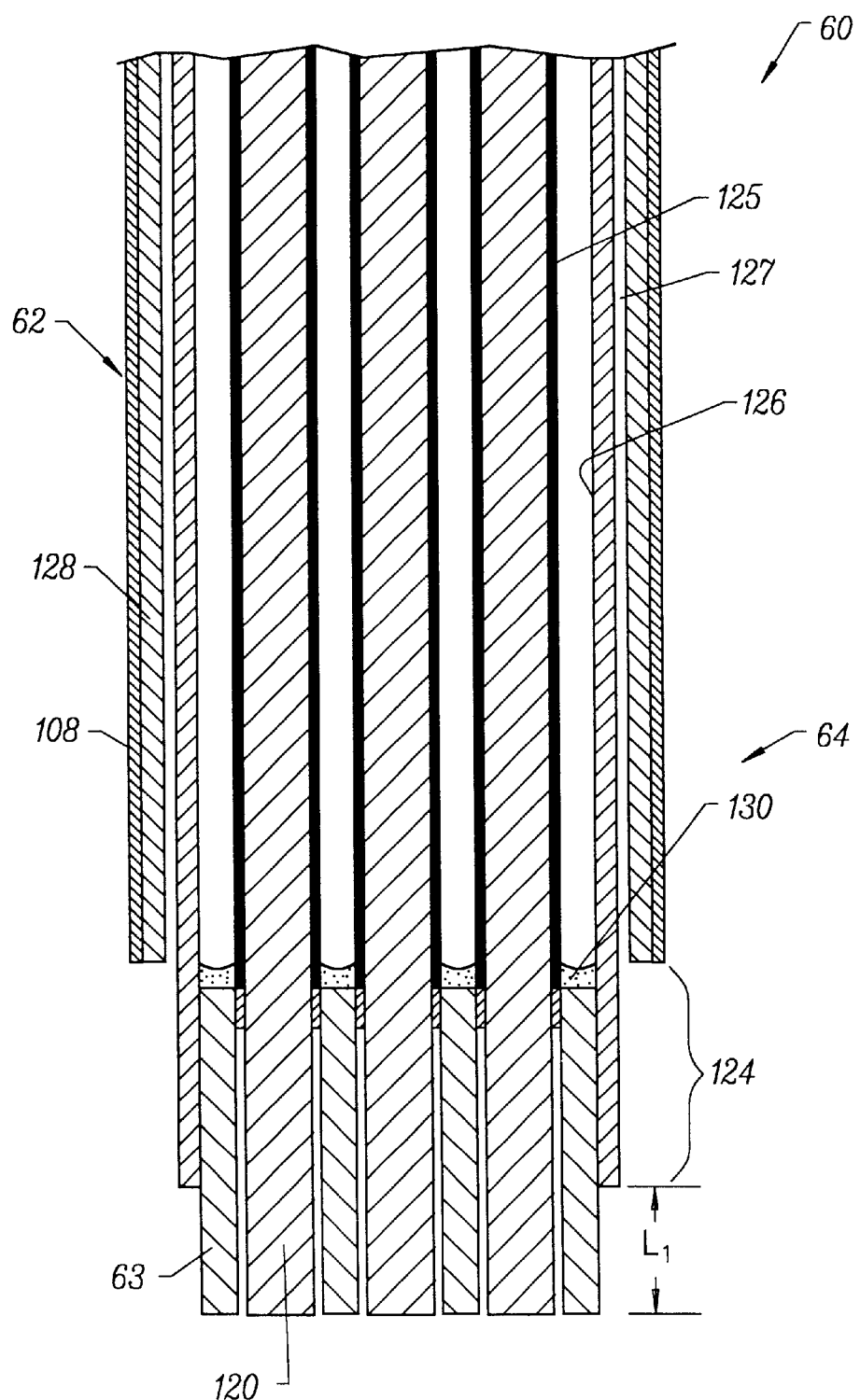
FIG. 2 is a cross-section view of a working end of a catheter according to one embodiment of the present invention.
Figure 3:
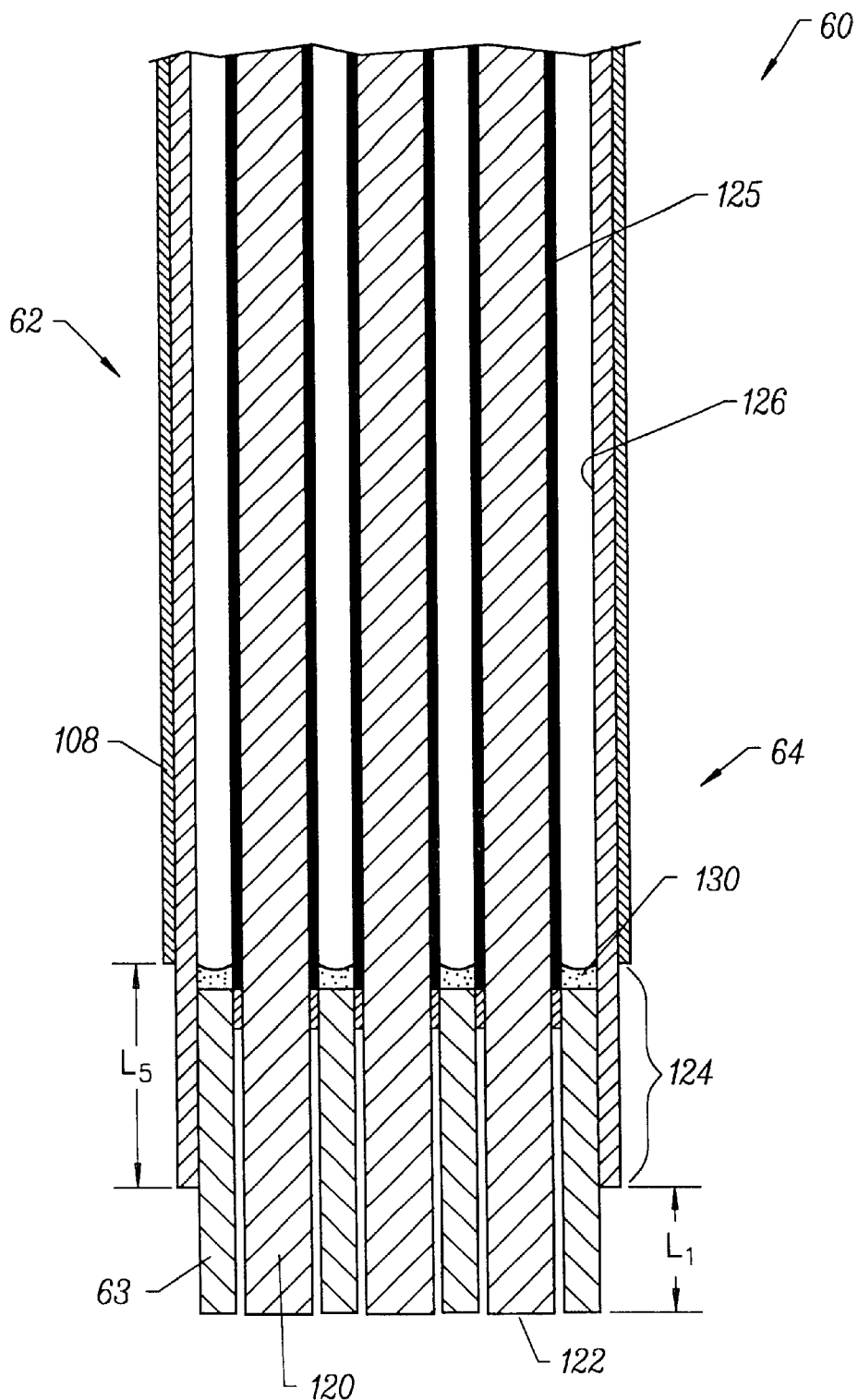
FIG. 3 is a cross-section view of a working end of a catheter according to a second embodiment of the present invention.

FIGS. 2 and 3 illustrate the working end 64 of an electrosurgical catheter 60 constructed according to the principles of the present invention. As shown in FIG. 2, catheter 60 generally includes an elongated shaft 62 which may be flexible or rigid, and an electrode support member 120 coupled to the distal end of shaft 62. Electrode support member 120 extends from the distal end of shaft 62 (usually about 1 to 20 mm), and provides support for a plurality of electrically isolated electrode terminals 63. Electrode support member 120 and electrode terminals 62 are preferably secured to a tubular support member 126 within shaft 60 by adhesive 130.

The electrode terminals 63 may be constructed using round, square, rectangular or other shaped conductive metals. By way of example, the electrode terminal materials may be selected from the group including stainless steel, tungsten and its alloys, molybdenum and its alloys, titanium and its alloys, nickel-based alloys, as well as platinum and its alloys. Electrode support member 120 is preferably a ceramic, glass or glass/ceramic composition (e.g., aluminum oxide, titanium nitride). Alternatively, electrode support member 120 may include the use of high-temperature biocompatible plastics such as polyether-ether-keytone (PEEK) manufactured by Vitrex International Products, Inc. or polysulfone manufactured by GE Plastics. The adhesive 130 may, by way of example, be an epoxy (e.g., Master Bond EP42HT) or a silicone-based adhesive.

Referring to FIG. 3, the electrically isolated electrode terminals 63 are spaced apart over tissue treatment surface 122 of electrode support member 120. The tissue treatment surface and individual electrode terminals 63 will usually have dimensions within the ranges set forth above. In the representative embodiment, the tissue treatment surface 122 has a circular cross-sectional shape with a diameter of about 0.5 to 5 mm (see FIG. 4). The individual electrode terminals 63 are preferably substantially flush with tissue treatment surface 122. Applicant has found that this configuration minimizes any sharp electrode edges and/or corners that would promote excessively high electric field intensities and associated current densities when a high frequency voltage is applied to the electrode terminals.

It should be noted that the electrode terminals 63 may protrude slightly outward from surface 122, typically by a distance from 0 mm to 2 mm, or the terminals may be recessed from this surface. For example, the electrode terminals 104 may be recessed by a distance from 0.01 mm to 1 mm, preferably 0.01 mm to 0.2 mm. In one embodiment of the invention, the electrode terminals are axially adjustable relative to the tissue treatment surface so that the surgeon can adjust the distance between the surface and the electrode terminals.

Figure 4:
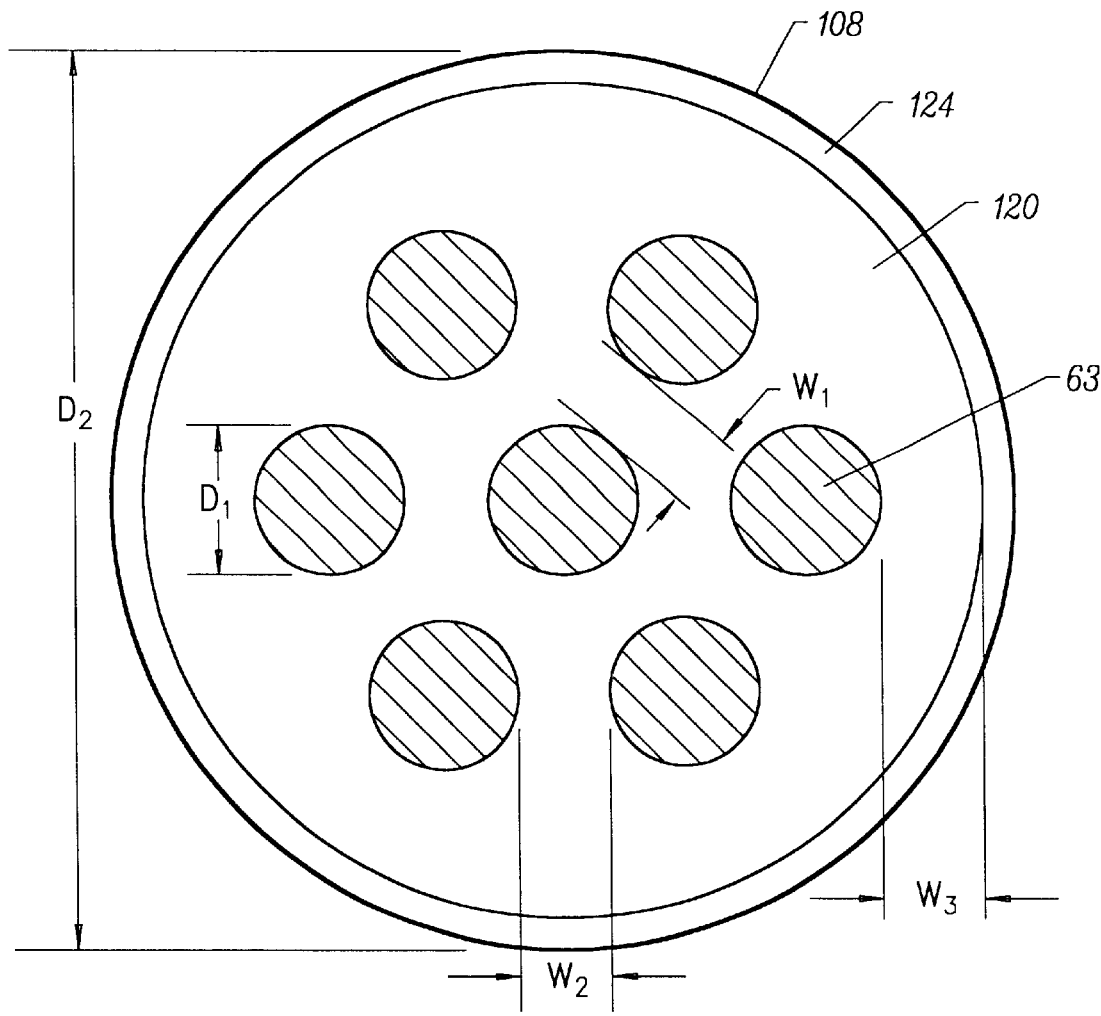
FIG. 4 is an end view of the catheter of FIG. 3.

In the first embodiment and referring to FIG. 4, a total of 7 circular active electrodes or electrode terminals 63 are shown in a symmetrical pattern having an active electrode diameter, $D_1$ in the range from 0.05 mm to 1.5 mm, more preferably in the range from 0.1 mm to 0.75 mm. The interelectrode spacings, $W_1$ and $W_2$ are preferably in the range from 0.1 mm to 1.5 mm and more preferably in the range from 0.2 mm to 0.75 mm. The distance between the outer perimeter of the electrode terminal 63 and the perimeter of the electrode support member, $W_3$ is preferably in the range from 0.1 mm to 1.5 mm and more preferably in the range from 0.2 mm to 0.75 mm. The overall diameter, $D_2$ of the working end 64 of catheter body 62 is preferably in the range from 0.5 mm to 10 mm and more preferably in the range from 1.0 mm to 5 mm. As discussed above, the shape of the active electrodes may be round (as shown in FIG. 4), square, triangular, hexagonal, rectangular, tubular, flat strip and the like and may be arranged in a circularly symmetric pattern as shown in FIG. 4 or may, by way of example, be arranged in a rectangular pattern, square pattern, or strip.

Referring again to FIG. 4, catheter body 62 includes a tubular cannula 126 extending along body 62 radially outward from support member 120 and electrode terminals 63. The material for cannula 126 may be advantageously selected from a group of electrically conductive metals so that the cannula 126 functions as both a structural support member for the array of electrode terminals 63 as well as a return electrode 124. The support member 126 is connected to an electrical lead wire (not shown) at its proximal end within a connector housing (not shown) and continues via a suitable connector to power supply 80 to provide electrical continuity between one output pole of high frequency generator 80 and said return electrode 124. The cannula 126 may be selected from the group including stainless steel, copper-based alloys, titanium or its alloys, and nickel-based alloys. The thickness of the cannula 126 is preferably in the range from 0.08 mm to 1.0 mm and more preferably in the range from 0.1 mm to 0.4 mm.

As shown in FIG. 2, cannula 126 is covered with an electrically insulating sleeve 108 to protect the patient's body from the electric current. Electrically insulating sleeve 108 may be a coating (e.g., nylon) or heat shrinkable plastic (e.g., fluropolymer or polyester). The proximal portion of the cannula 126 is left exposed to function as the return electrode 124. The length of the return electrode 124, $L_5$ is preferably in the range from 1 mm to 30 mm and more preferably in the range from 2 mm to 20 mm. The spacing between the most distal portion of the return electrode 124 and the plane of the tissue treatment surface 122 of the electrode support member 120, $L_1$ is preferably in the range from 0.5 mm to 30 mm and more preferably in the range from 1 mm to 20 mm. The thickness of the electrically insulating sleeve 108 is preferably in the range from 0.01 mm to 0.5 mm and more preferably in the range from 0.02 mm to 0.2 mm.

As shown in FIG. 2, return electrode 124 is not directly connected to electrode terminals 63. To complete this current path so that electrode terminals 63 are electrically connected to return electrode 124, electrically conducting fluid (e.g., isotonic saline) is caused to flow therebetween. In the representative embodiment, the fluid path is formed in catheter by an inner lumen 127 or annular gap between the return electrode 124 and a second tubular support member 128 within shaft 60. This annular gap may be formed near the perimeter of the shaft 60 as shown in FIG. 2 such that the electrically conducting fluid tends to flow radially inward towards the target site, or it may be formed towards the center of shaft 60 (not shown) so that the fluid flows radially outward. In both of these embodiments, a fluid source (e.g., a bag of fluid elevated above the surgical site or having a pumping device), is coupled to catheter 60 via a fluid supply tube (not shown) that may or may not have a controllable valve. A more complete description of an electrosurgical probe incorporating one or more fluid lumen(s) can be found in U.S. Pat. No. 5,697,281, previously been incorporated by reference.

In an alternative embodiment shown in FIG. 3, the electrically conducting fluid is delivered from a fluid delivery element (not shown) that is separate from catheter 60. In arthroscopic surgery, for example, the body cavity will be flooded with isotonic saline and the probe 20 will be introduced into this flooded cavity. Electrically conducting fluid will be continually resupplied to maintain the conduction path between return electrode 124 and electrode terminals 63.

Figure 5A:
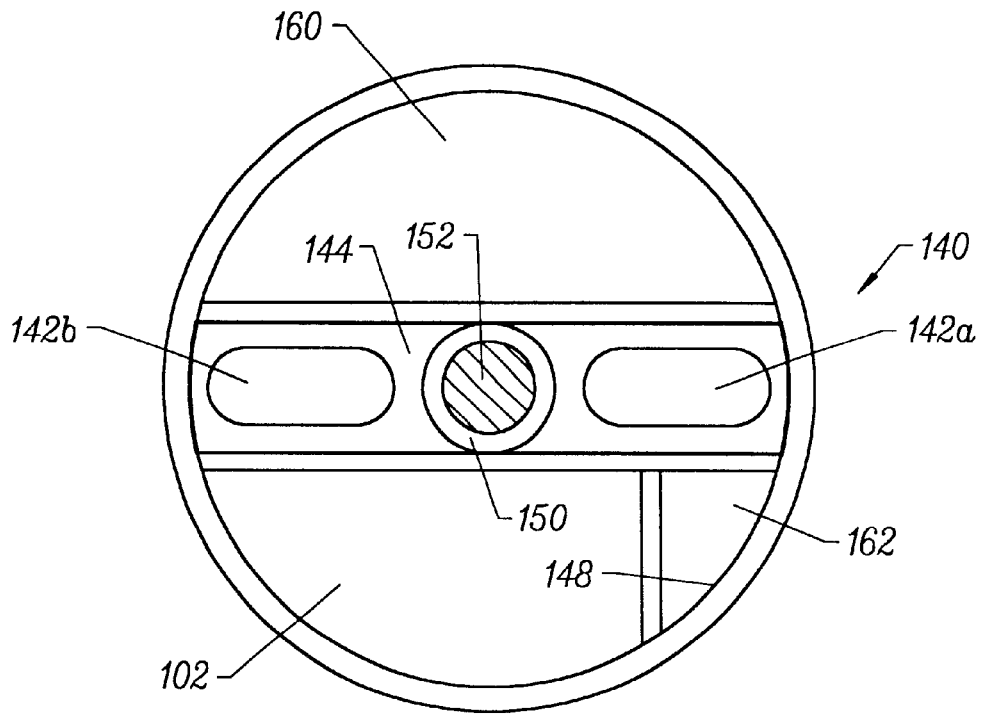
FIGS. 5A and 5B are end and cross-sectional views, respectively of a third embodiment of a catheter.
Figure 5B:
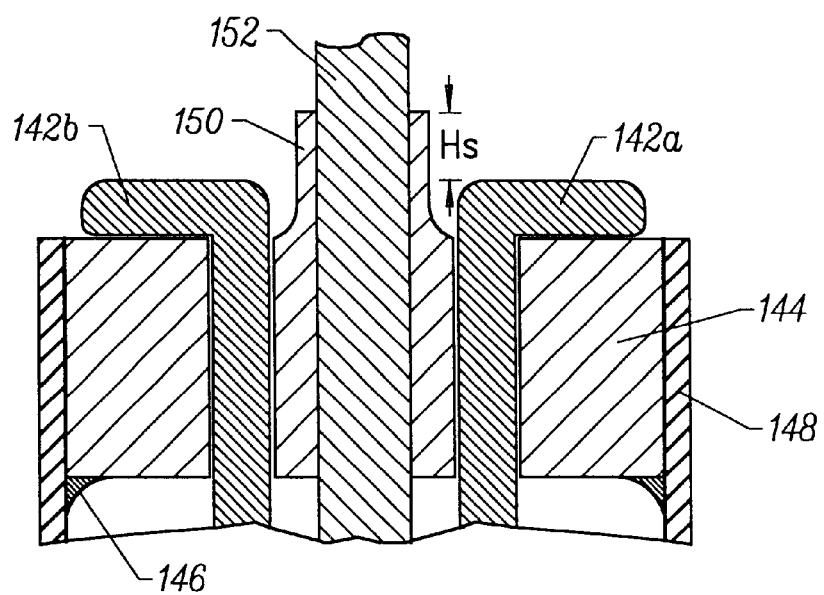

FIGS. 5–7 additional embodiments of a catheter particularly designed for ablation or volumetric removal of tissue. As shown in FIG. 5A, a tissue ablation region 140 of catheter 60 includes two active electrodes 142a, 142b, secured within an electrically insulating support member 144. The electrodes 142a, 142b are preferably composed of a refractory, electrically conductive metal or alloy, such as platinum, titanium, tantalum, tungsten, stainless steel and the like. The support member 144 is secured to the distal end of catheter 60 with a biocompatible adhesive 146 between support member 144 and outer sleeve 148 (see FIG. 5B). An inorganic electrically insulating sleeve 150 preferably extends above the distal plane of active electrodes 142a, 142b by a distance $H_S$. A central lumen in sleeve 150 provides a passageway for a guide wire 152 that permits axial displacement and rotation of tissue ablating region 140 relative to guide wire 152.

In an exemplary embodiment, the support member 144 will comprise an inorganic insulator, such as ceramic, glass, glass/ceramic or a high resistivity material, such as silicon or the like. An inorganic material is generally preferred for the construction of the support member 1444 since organic or silicone based polymers are known to rapidly erode during sustained periods of the application of high voltages between electrodes 142 and the return electrode 151 during tissue ablation. However, for situations in which the total cumulative time of applied power is less than about one minute, organic or silicone based polymers may be used without significant erosion and loss of material of the support member 144 and, therefore, without significant reduction in ablation performance. As shown in FIG. 5A, an irrigation lumen 160 and one or more aspiration lumen(s) 162 are provided to inject electrically conducting fluid and remove gaseous products of ablation from the target site.

Figure 6A:
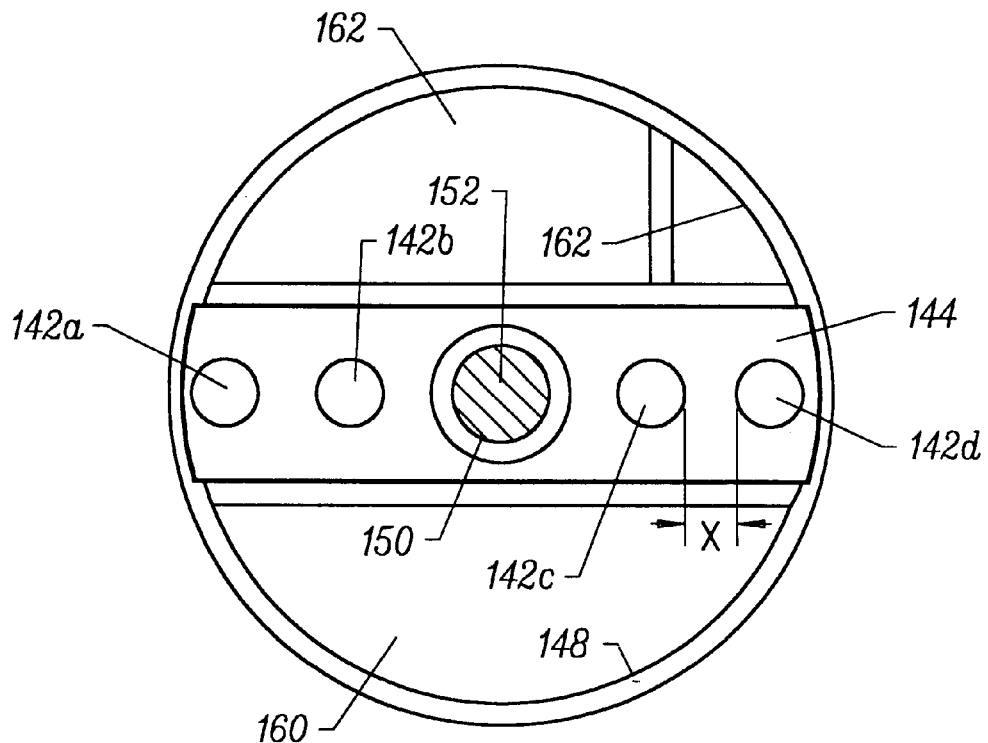
FIGS. 6A and 6B are end and cross-sectional views, respectively of a fourth embodiment of a catheter.
Figure 6B:
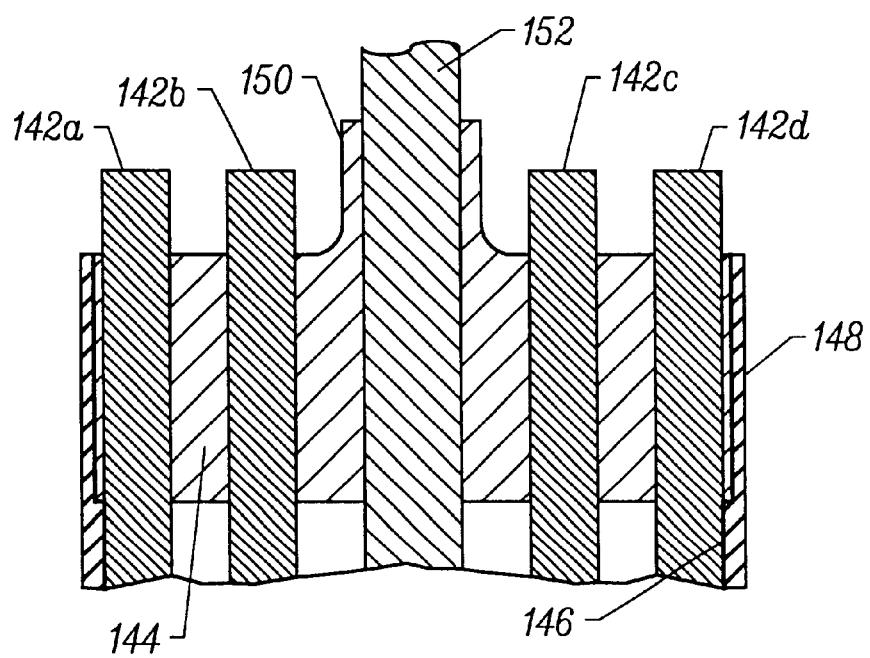

Referring now to FIGS. 6A and 6B, a second embodiment of tissue ablation region 140 of catheter 60 will now be described. In this embodiment, four active electrodes 142a, 142b, 142c, 142d are secured within an inorganic electrically insulating support member 144. Similar to the previous embodiment, support member 144 is secured to the distal end of catheter 60 with a biocompatible adhesive 146 between support member 144 and outer sleeve 148. An inorganic electrically insulating sleeve 150 preferably extends above the distal plane of active electrodes 142 by a distance $H_S$. A central lumen in support member 144 provides a passageway for guide wire 152 that permits axial displacement and rotation of tissue ablating region 140 relative to guide wire 152. As shown in FIG. 6A, an irrigation lumen 154 and an aspiration lumen 156 are provided to inject electrically conducting fluid and remove gaseous products of ablation from the target site.

Figure 7A:
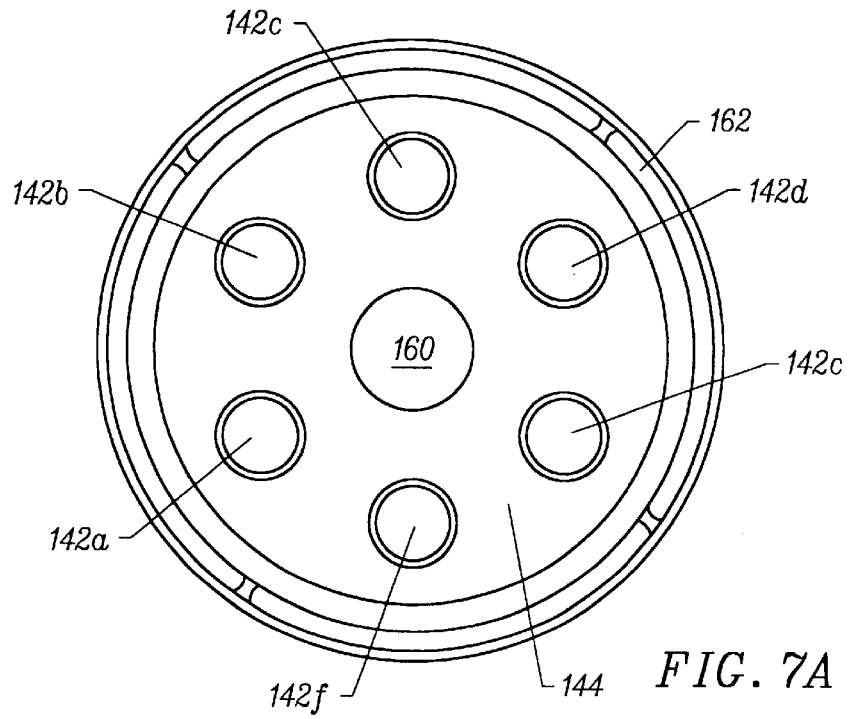
FIGS. 7A and 7B are end and cross-sectional views, respectively of a fifth embodiment of a catheter.
Figure 7B:
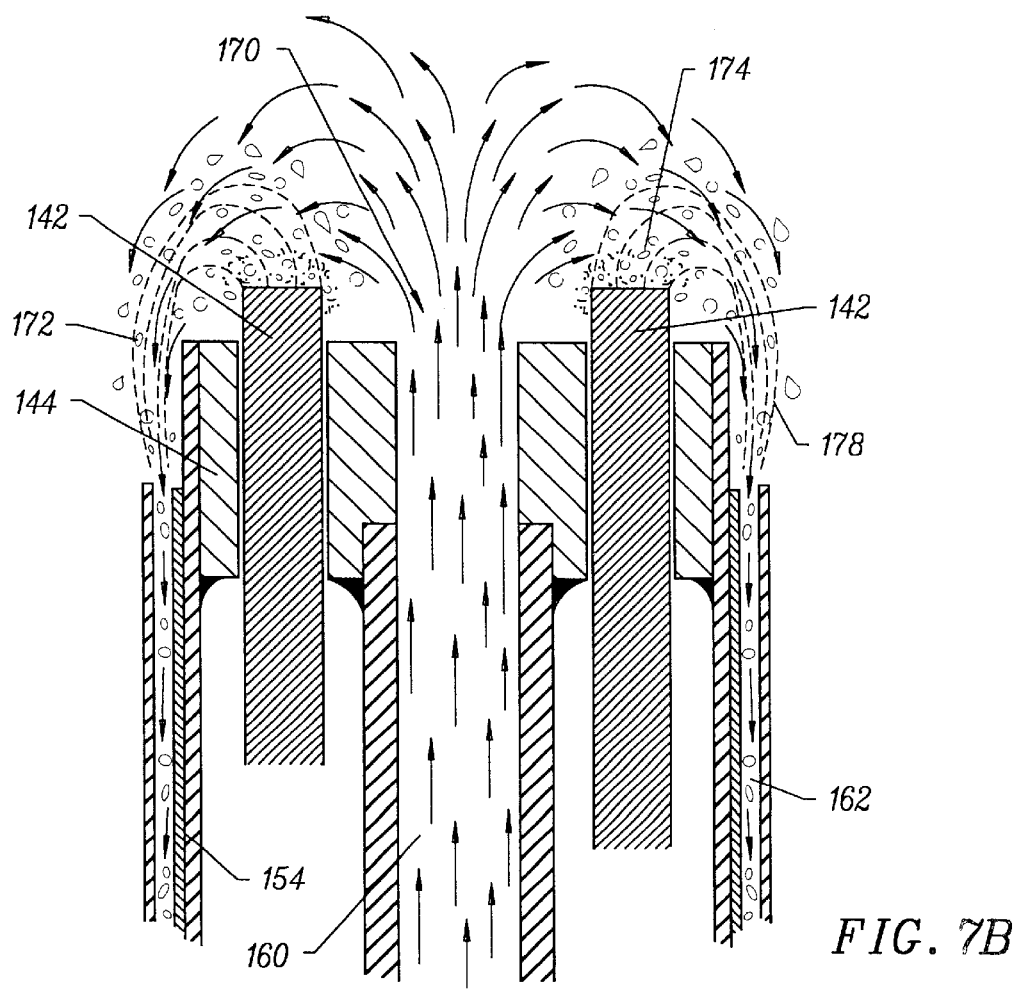

FIGS. 7A and 7B illustrate another embodiment of an ablation catheter incorporating six active electrodes 142a–142f secured within inorganic support member 144. A return electrode 154 (e.g., metal sleeve) is positioned proximal to the active electrodes 142a–42f by a distance $H_X$. As shown in FIG. 7B, an annular aspiration lumen 162 and a central irrigation lumen 160 are provided to inject electrically conducting fluid 170 and remove gaseous products of ablation 172 from the target site. When high frequency voltage is applied between the return electrode 154 and active electrodes 142, a vapor layer 174 forms at and around active electrodes 142 with concomitant volumetric removal (ablation) of the target tissue. The target tissue is decomposed into gaseous products of ablation 172 which are entrained in electrically conducting fluid 170 and evacuated through aspiration lumen 162. In this embodiment, current flux lines 178 travel proximally from the distal tips of electrodes 142 to the proximally spaced return electrode 154.

Figure 8:
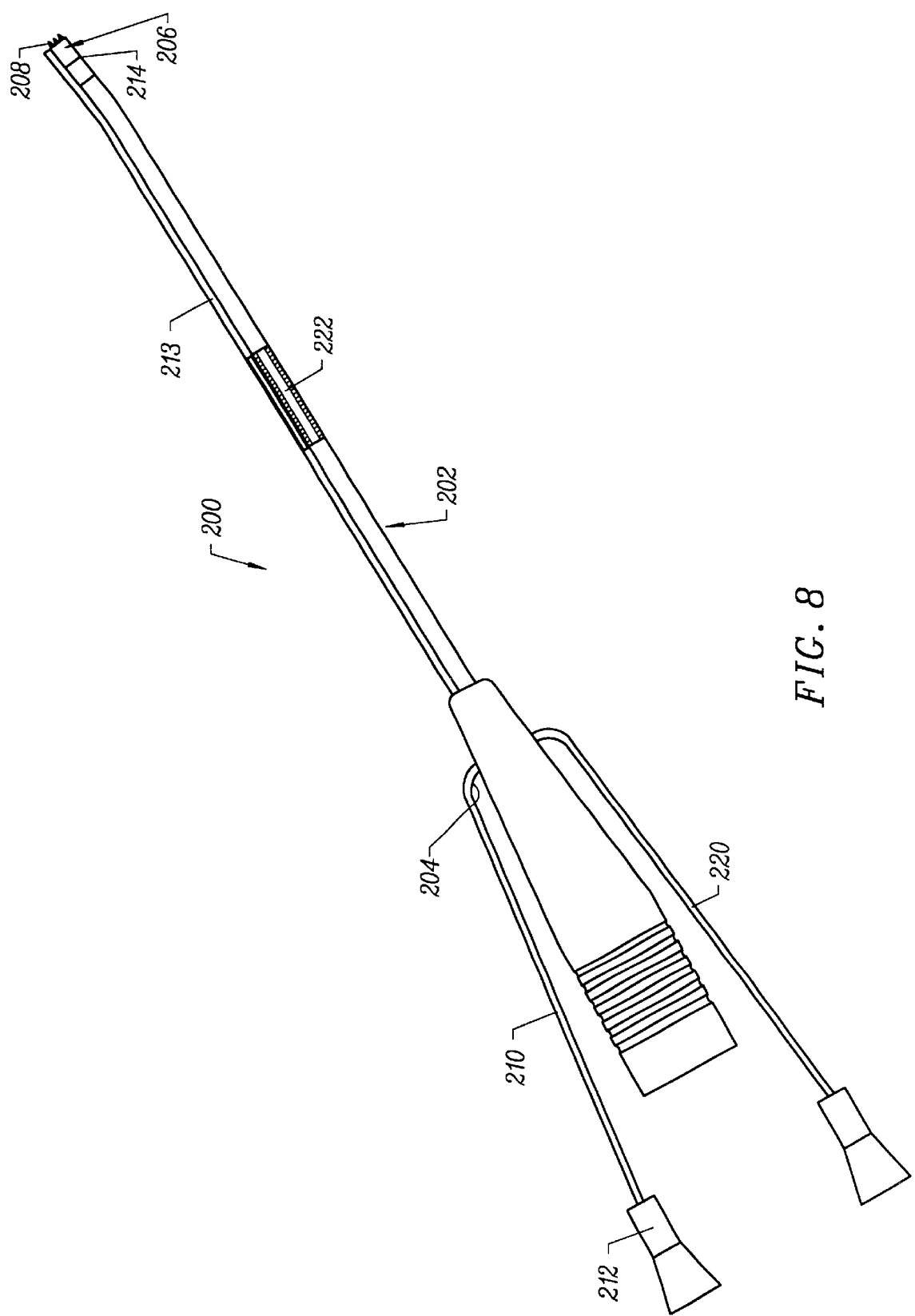
FIG. 8 is a perspective view an electrosurgical probe according to the present invention.

FIGS. 8–10 and 16 illustrate electrosurgical probes 200 constructed according to the principles of the present invention for treatment of body structures in the gastrointestinal tract. As shown in FIG. 8, probe 200 generally includes an elongated shaft 202 which may be flexible or rigid, a handle 204 coupled to the proximal end of shaft 202 and an electrode support member 206 coupled to the distal end of shaft 202. Shaft 202 preferably comprises a plastic material that is easily molded into the shape shown in FIG. 8. In an alternative embodiment (not shown), shaft 202 comprises an electrically conducting material, usually metal, which is selected from the group comprising tungsten, stainless steel alloys, platinum or its alloys, titanium or its alloys, molybdenum or its alloys, and nickel or its alloys. In this embodiment, shaft 202 includes an electrically insulating jacket (not shown), which is typically formed as one or more electrically insulating sheaths or coatings, such as polytetrafluoroethylene, polyimide, and the like. The provision of the electrically insulating jacket over the shaft prevents direct electrical contact between these metal elements and any adjacent body structure or the surgeon. Such direct electrical contact between a body structure (e.g., tendon) and an exposed electrode could result in unwanted heating and necrosis of the structure at the point of contact causing necrosis.

Handle 204 typically comprises a plastic material that is easily molded into a suitable shape for handling by the surgeon. Handle 204 defines an inner cavity (not shown) that houses the electrical connections, and provides a suitable interface for connection to an electrical connecting cable. Electrode support member 206 extends from the distal end of shaft 202 (usually about 1 to 20 mm), and provides support for a plurality of electrically isolated electrode terminals 208. As shown in FIG. 8, a fluid tube 210 extends through an opening in handle 204, and includes a connector 212 for connection to a fluid supply source, for supplying electrically conductive fluid to the target site. Depending on the configuration of the distal surface of shaft 202, fluid tube 210 may extend through a single lumen (not shown) in shaft 202, or it may be coupled to a plurality of lumens (also not shown) that extend through shaft 202 to a plurality of openings at its distal end. In the representative embodiment, fluid tube 210 is coupled to an distal tube 213 that extends along the exterior of shaft 202 to a point just proximal of return electrode 214.

Probe 200 further includes an aspiration tube 220 adapted for connection to a source of vacuum for aspirating excess fluid, products of ablation and other media from the target site. Aspiration tube 220 is fluidly coupled to an inner lumen 222 within shaft 202, which extends to a proximal opening (not shown in FIG. 8) in electrode support member 206. Aspirating the electrically conductive fluid during surgery allows the surgeon to see the target site, and it prevents the fluid from flowing into the patient's body. This aspiration should be controlled, however, so that the conductive fluid maintains a conductive path between the active electrode terminal(s) and the return electrode. In some embodiments, the probe 200 will also include one or more aspiration electrode(s) (not shown) coupled to the aspiration lumen 222 for inhibiting clogging during aspiration of tissue fragments from the surgical site. A more complete description of these embodiments can be found in commonly assigned co-pending application Ser. No. 09/010,382, filed Jan. 21, 1998, the complete disclosure of which is incorporated herein by reference for all purposes.

In the embodiment shown in FIG. 8, return electrode 214 preferably comprises an annular conductive band coupled to the distal end of shaft 202 slightly proximal to a tissue treatment surface 216 of electrode support member 206, typically about 0.5 to 10 mm and more preferably about 1 to 10 mm. Return electrode 214 is coupled to a connector (not shown) that extends to the proximal end of probe 200, where it is suitably connected to power supply 80 (FIG. 1).

Figure 9:
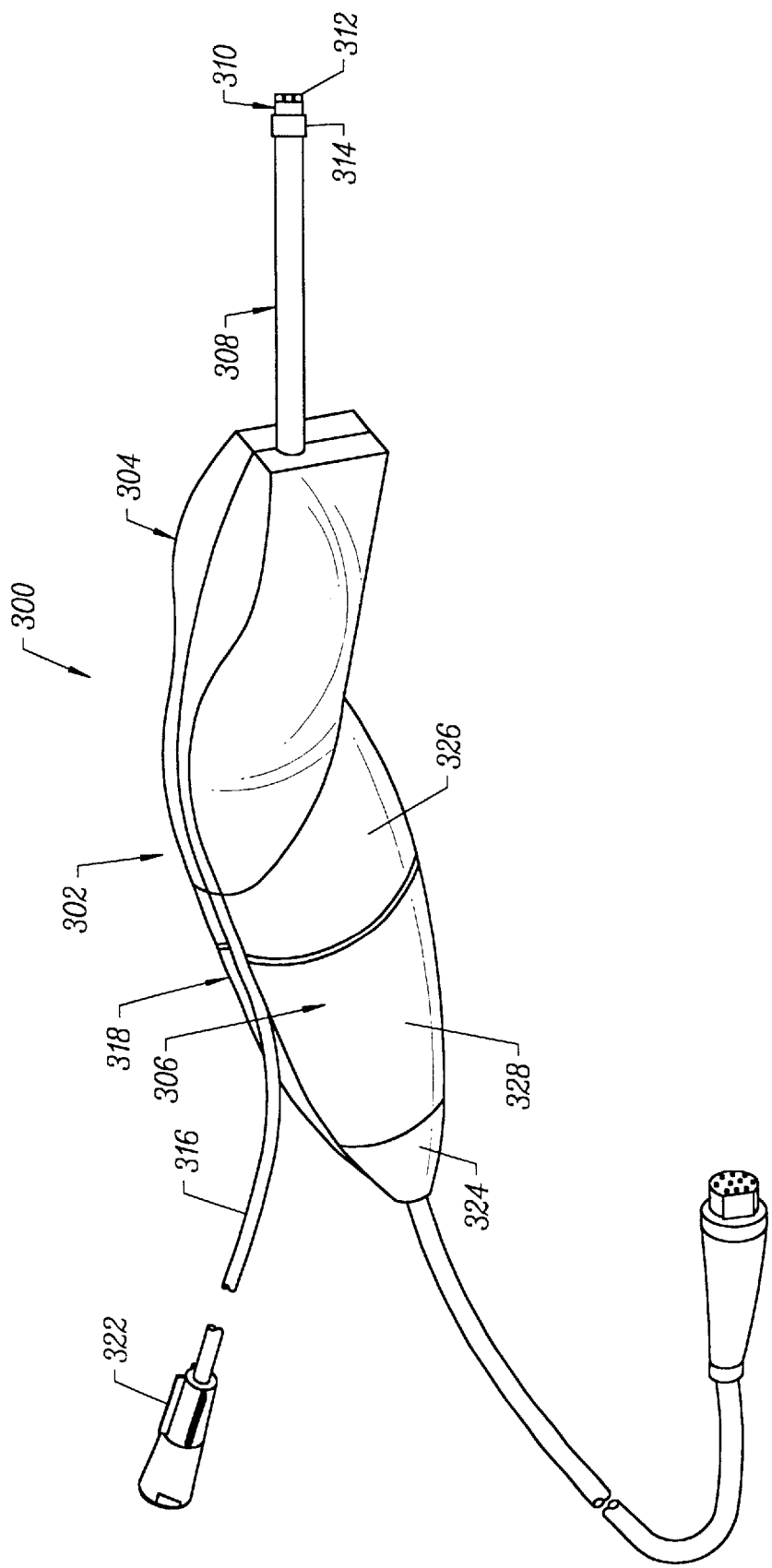
FIG. 9 is a perspective view of an electrosurgical probe particularly designed for forming holes or channels in tissue according to the present invention.
Figure 10:
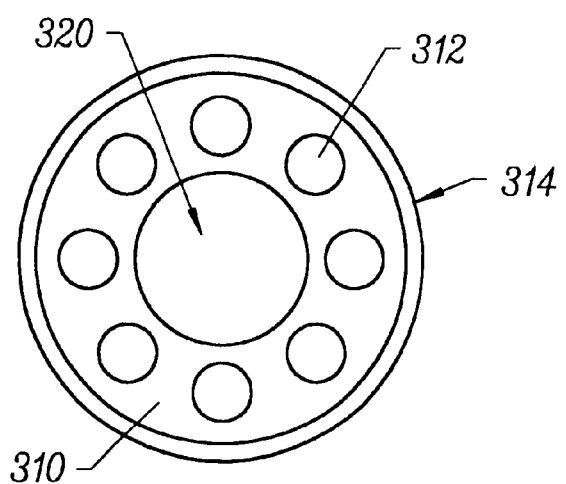
FIG. 10 is an end view of the probe of FIG. 9.

Referring now to FIGS. 9 and 10, an exemplary electrosurgical probe 300 for removing small holes or channels of tissue will now be described. As shown, probe 300 comprises a handle 302, which preferably comprises a disposable distal portion 304 removably coupled to a proximal reusable portion 306, and an elongate shaft 308 extending from distal portion 304 of handle 302. Shaft 308 is also disposable, and preferably removably coupled to distal portion 304 of the handle. The proximal and distal portions of handle 302 typically comprise a plastic material that is easily molded into a suitable shape for handling by the surgeon. Handle 302 defines an inner cavity (not shown) that houses the electrical connections (also not shown), and provides a suitable interface for connection to power supply 80 (FIG. 1). In the exemplary embodiment, the proximal portion of handle 302 is constructed so that it can be re-used by sterilizing handle 302 between surgical procedures. However, it should be understood that both the proximal and distal portions of the handle may be reusable, or both of these handle portions may be disposable, if desired.

Shaft 308 is preferably sized to provide endoscopic access to the nasal cavity. Accordingly, shaft 308 preferably has a length in the range of about 4 to 25 cm and a diameter less than 1 cm. In the exemplary embodiment, shaft 308 is also preferably sized for forming small holes or channels in tissue and, therefore, will have a diameter less than 3 mm, preferably less than about 1 mm. Alternatively, shaft 308 may have a distal portion that is smaller than the rest of shaft for forming such holes. As shown in FIG. 9, shaft 308 includes an electrically insulating electrode support member 310 extending from its distal end (usually about 0.5 to 20 mm) to provide support for a plurality of electrically isolated electrode terminals 312. Alternatively, electrode support member 310 may be recessed from the distal end of shaft 308 to help confine the electrically conductive fluid around the electrode terminals 312 during the surgical procedure, as discussed above.

In the embodiment shown in FIGS. 9 and 10, probe 300 includes an annular return electrode 314 for completing the current path between electrode terminals 312 and high frequency power supply 80. Return electrode 314 is spaced proximally from electrode terminal(s) 312 a sufficient distance to avoid arcing therebetween. In addition, return electrode 314 is positioned such that, when electrode terminal(s) 312 are brought adjacent a tissue structure, return electrode 314 is spaced away from the tissue structure so that the tissue structure cannot, at least by itself, complete the current flow path between electrode terminal(s) 312 and return electrode 314.

Similar to previous embodiments, probe 300 includes a fluid tube 316 for delivering electrically conductive fluid to the target site. Fluid tube 316 is sized to extend through a groove 318 in handle 302 and through an inner cavity (not shown) in shaft 308 to a distal opening 320 (FIG. 10) located adjacent electrode support member 310. Tube 316 preferably extends all the way through the inner cavity to opening 320 to eliminate any possible fluid ingress into the cavity. As shown in FIG. 9, fluid tube 316 includes a proximal connector 322 for coupling to an electrically conductive fluid source (see FIG. 1). Probe 300 will also include a valve or equivalent structure for controlling the flow rate of the electrically conducting fluid to the target site. In the representative embodiment, handle 302 comprises a main body 324, 326 and a rotatable sleeve 328 for controlling fluid flow through tube 316. Rotation of sleeve 328 crimps tube 316 to limit or complete shut off flow therethrough. Of course, this fluid control may be provided by a variety of other input and valve devices, such as switches, buttons, etc.

In alternative embodiments, the fluid path may be directly formed in probe 300 by, for example, a central inner lumen or an annular gap (not shown) within the handle and the shaft. This inner lumen may be formed near the perimeter of the probe 300 such that the electrically conducting fluid tends to flow radially inward towards the target site, or it may be formed towards the center of probe 300 so that the fluid flows radially outward. In addition, the electrically conducting fluid may be delivered from a fluid delivery element (not shown) that is separate from probe 300.

Referring to FIG. 10, electrically isolated electrode terminals 312 are circumferentially spaced around fluid opening 320 at the tissue treatment surface of electrode support member 306. In the representative embodiment, the tissue treatment surface has a circular cross-sectional shape with a diameter of about 0.2 to 3 mm, usually less than 1 mm. The individual electrode terminals 312 have the dimensions described above, and preferably extend about 0.05 to 4.0 mm from the tissue treatment surface. Of course, the electrode terminals 312 may be substantially flush with the tissue treatment surface or the terminals may be recessed from this surface. For example, the electrode terminals 312 may be recessed by a distance from 0.01 mm to 1 mm, preferably 0.01 mm to 0.2 mm. In one embodiment of the invention, the electrode terminals are axially adjustable relative to the tissue treatment surface so that the surgeon can adjust the distance between the surface and the electrode terminals.

Figure 16:
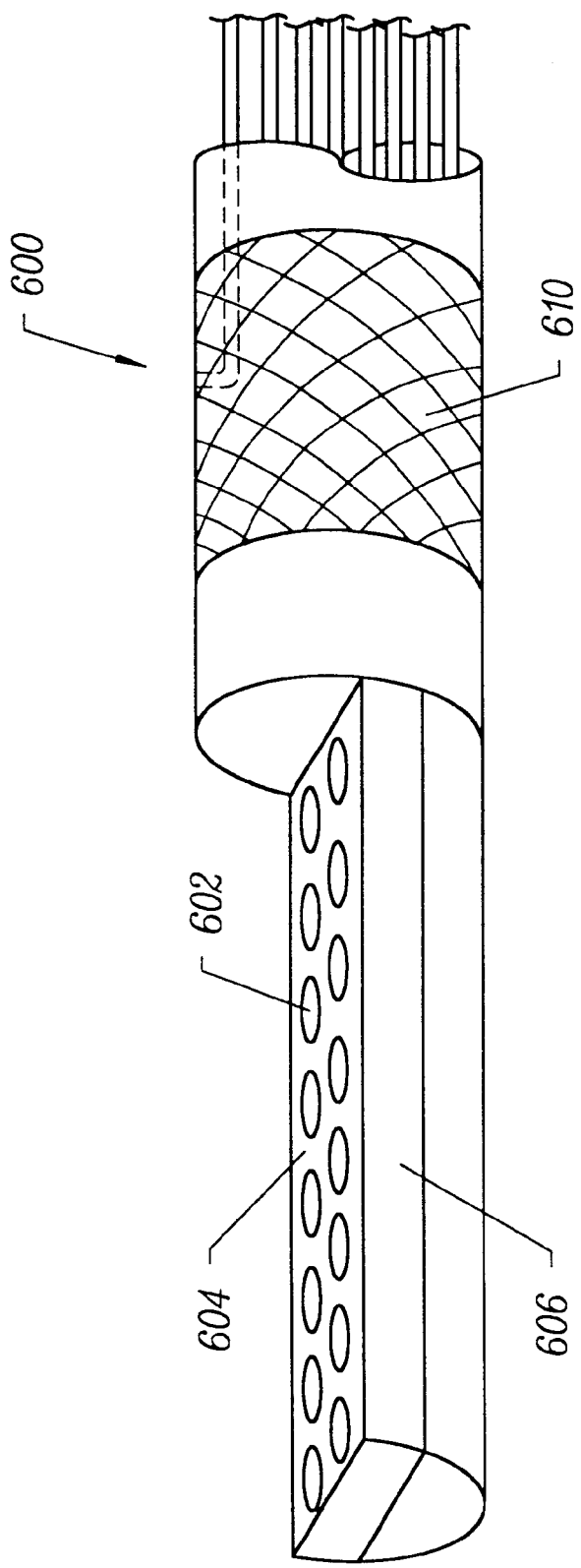
FIG. 16 illustrates another embodiment of the present invention incorporating side facing electrode terminals.

Referring now to FIG. 16, an alternative electrosurgical probe 600 incorporates a plurality of electrode terminals 602 on a lateral or recessed surface 604 of the probe 600. As shown, the electrode terminals 602 are spaced apart over lateral surface 604, and preferable protrude outward from surface 604 by about 0 to 2 mm, usually about 0 mm, or substantially flush with lateral surface 604. Electrode terminals which are flush with the surface, or protrude over a minimum distance, will provide less aggressive ablation and are particularly suitable for effecting contraction of collagen fibers within underlying tissue. As shown, electrode terminals 602 are preferably anchored in an electrically insulated support matrix 606. Similar to previous embodiments, a return electrode 610 is located on the exterior of the shaft of probe 600, preferably spaced about 1 mm to 10 mm proximally from lateral surface 604.

Figure 11:
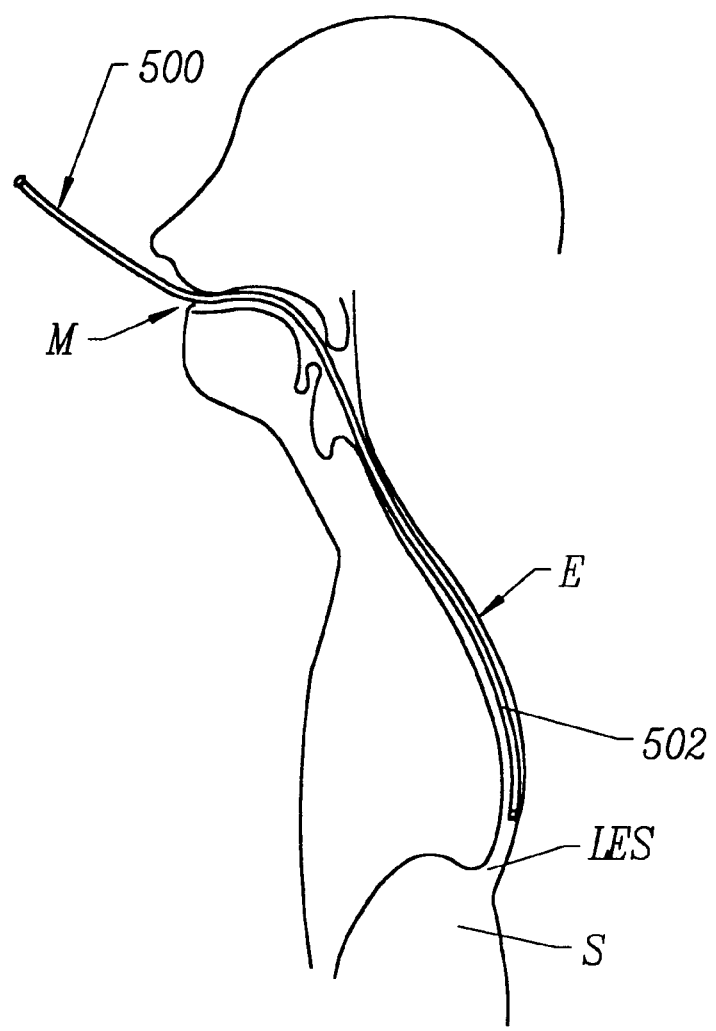
FIG. 11–13 illustrate a method for applying electrical energy to the lower sphincter to treat gastroesophageal reflux.

The present invention is particularly useful in treating gastroesophageal reflux by applying electrical energy to the lower sphincter to improve its tone (i.e., to stiffen the lower sphincter). Referring now to FIGS. 11–15, methods for applying electrical energy to the lower sphincter according to the present invention will now be described. As shown in FIG. 11, a working end 64 of an electrosurgical catheter 60 is advanced through the patient's mouth M and throat and down the esophagus E to the lower sphincter LES, which sits at the junction of the esophagus E and the stomach S. Of course, the working end 64 of an electrosurgical instrument may be advanced to the LES in a variety of different manners, e.g., through a percutaneous or open penetration in the patient, transluminally through a blood vessel, etc.

Figure 12:
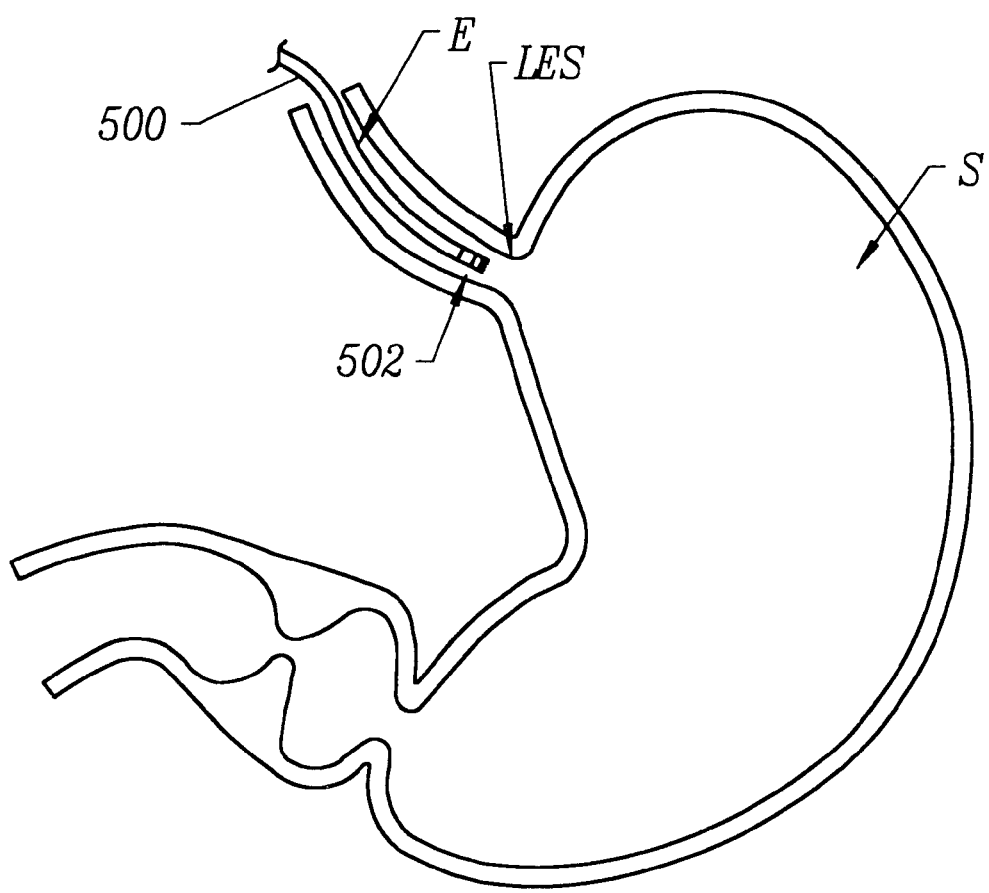
Figure 13:
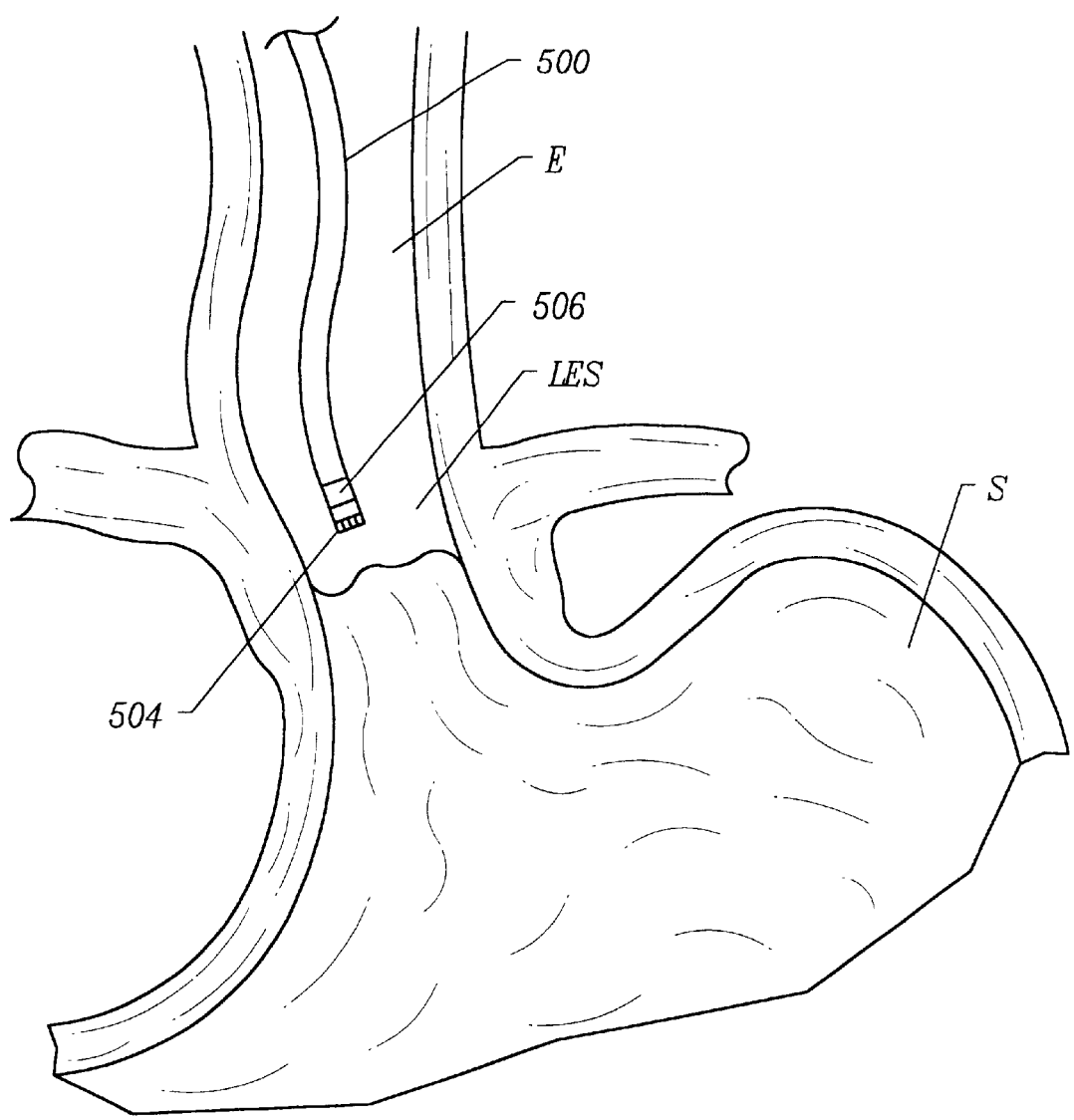

Referring now to FIGS. 12 and 13, working end 64 is advanced such that one or more electrode terminal(s) 63 are positioned adjacent to the LES. In the preferred embodiment, electrically conductive fluid 509 is delivered through catheter 60 to the electrode terminal(s) 63 (see FIGS. 14 and 15). The fluid flows past a return electrode 65, which is usually located on the catheter proximal to the electrode terminal(s) 64. The rate of fluid flow is controlled with valve (not shown) such that the zone between the tissue and electrode terminal(s) 63 is constantly immersed in the fluid. The power supply 80 is then turned on and adjusted such that a high frequency voltage difference is applied between electrode terminals 63 and return electrode 65. The electrically conductive fluid 509 (see FIGS. 14 and 15) provides the conduction path between electrode terminals 63 and the return electrode 65. Once the catheter 60 has been activated, the surgeon will positioned the electrode terminals 60 in contact with, or close proximity to, the LES to either shrink collagen fibers in the LES or to volumetrically remove portions of the LES.

Figure 14:
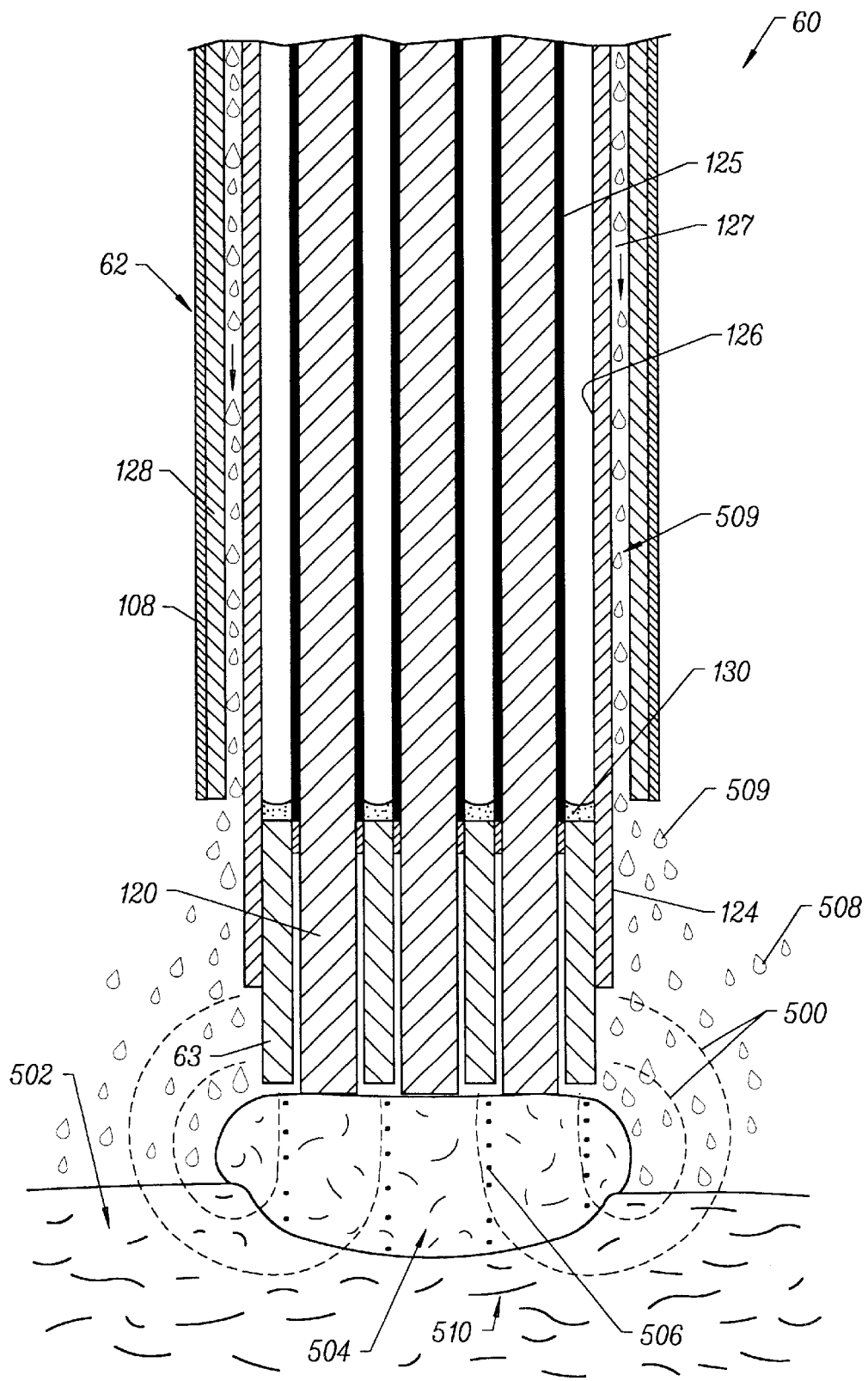
FIG. 14 is a more detailed view illustrating a method of volumetrically removing tissue according to the present invention.

FIG. 14 illustrates the volumetric removal (e.g., ablation) of tissue in more detail. Note that electrode terminals 63 preferably extend beyond the distal surface of electrode support member 120 for this application to increase the current density at the tips of the electrode terminals, which facilitates transition into the ablation mode. As shown, a high frequency voltage difference is applied between electrode terminal(s) 63 and return electrode 124 such that electric current 500 flows through the conductive fluid 509. The high frequency voltage is sufficient to convert the electrically conductive fluid (not shown) between the target tissue 502 and electrode terminal(s) 63 into an ionized vapor layer 504 or plasma. As a result of the applied voltage difference between electrode terminal(s) 63 and the target tissue 502 (i.e., the voltage gradient across the plasma layer 504), charged particles 506 in the plasma (viz., electrons) are accelerated towards the tissue. At sufficiently high voltage differences, these charged particles 506 gain sufficient energy to cause dissociation of the molecular bonds within tissue structures. This molecular dissociation is accompanied by the volumetric removal (i.e, ablative sublimation) of tissue and the production of low molecular weight gases 508, such as oxygen, nitrogen, carbon dioxide, hydrogen and methane. The short range of the accelerated charged particles 506 within the tissue confines the molecular dissociation process to the surface layer to minimize damage and necrosis to the underlying tissue 510.

During the process, the gases 508 may be aspirated through a suction tube, instrument or lumen with shaft (not shown) suitably coupled to a vacuum source. In addition, excess electrically conductive fluid, and other fluids (e.g., blood) may be aspirated from the target site to facilitate the surgeon's view. During ablation of the tissue, the residual heat generated by the current flux lines 500 (typically less than 150° C.), will usually be sufficient to coagulate any severed blood vessels at the site. If not, the surgeon may switch the power supply 80 into the coagulation mode by lowering the voltage to a level below the threshold for fluid vaporization, as discussed above. This simultaneous hemostasis results in less bleeding and facilitates the surgeon's ability to perform the procedure.

Depending on the procedure, the surgeon may translate the electrode terminals 63 relative to the LES tissue to form holes, channels, stripes, divots, craters or the like within the LES. In addition, the surgeon may purposely create some thermal damage within these holes, or channels to form scar tissue that will inhibit the LES from swelling after the procedure. In one embodiment, the physician axially translates the electrode terminals 63 into the LES tissue as the tissue is volumetrically removed to form one or more holes in the LES, typically having a diameter of less than 2 mm, preferably less than 1 mm. In another embodiment, the physician translates the electrode terminals 58 across the outer surface of the LES to form one or more channels or troughs. Applicant has found that the present invention can quickly and cleanly create such holes, divots or channels in tissue with the cold ablation technology described herein. A more complete description of methods for forming holes or channels in tissue can be found in U.S. Pat. No. 5,683,366, the complete disclosure of which is incorporated herein by reference for all purposes.

Figure 15:
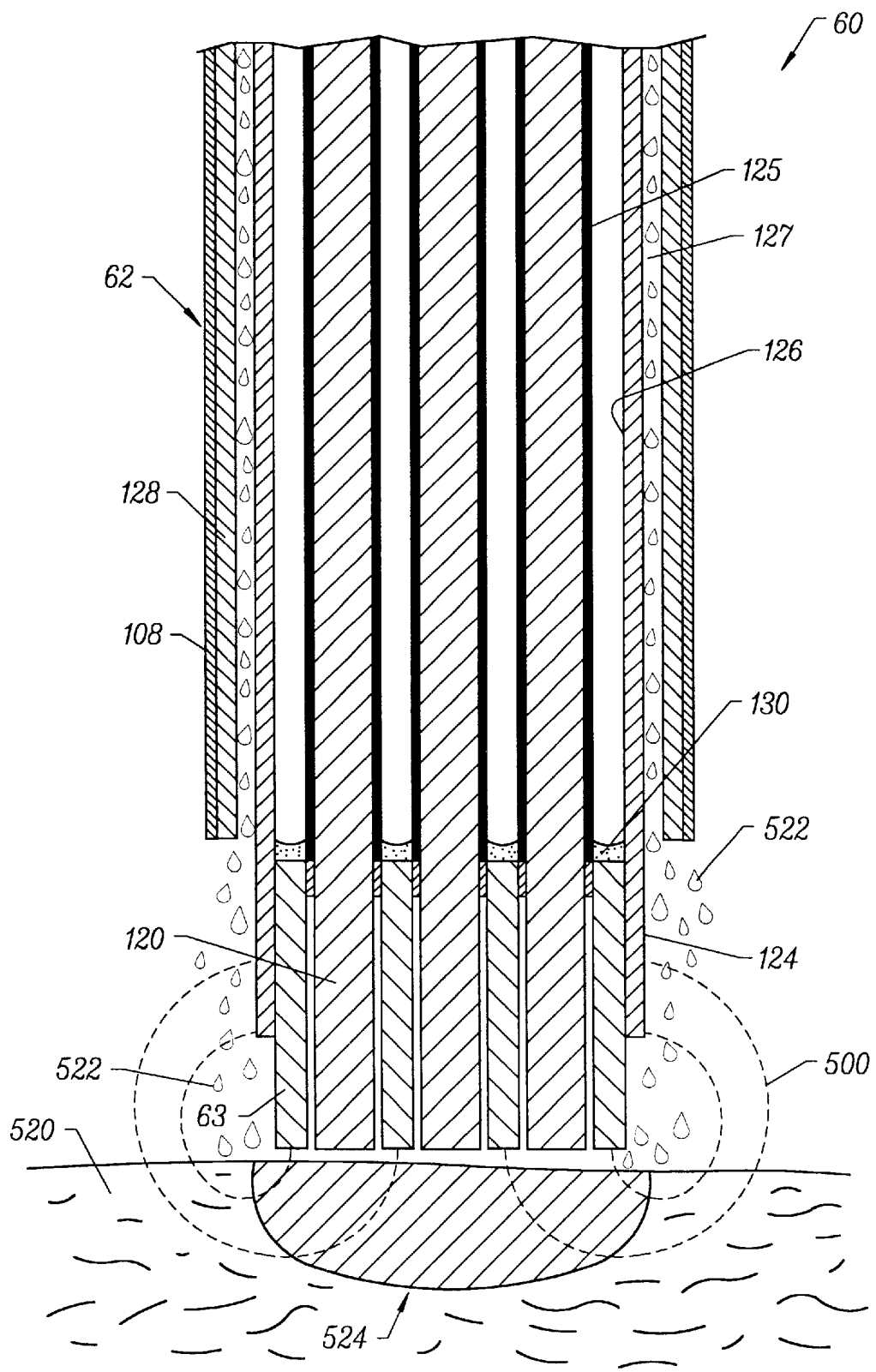
FIG. 15 is a more detailed view illustrating a method of contracting collagen fibers within tissue according to the present invention.

Referring now to FIG. 15, a method for contracting collagen fibers with the LES will now be shown in detail. When a voltage is applied between the electrode terminals 63 and the return electrode 124, electrical current flows along current flux lines 500. The current flux lines 520 flow a short distance, $L_4$, into the surface of tissue 520 and through the electrically conductive fluid 522 in the region above the surface of the tissue to complete the electrical path between the electrode terminals 63 and the return electrode 124. As a consequence of the electrical impedance of the tissue and the proper selection of the applied voltage and current, heating of the tissue 520 occurs in a region 524 (shaded) below the surface of the tissue 520, said heating elevating the temperature of the tissue from normal body temperature (e.g. 37° C.) to a temperature in the range 55° C. to 85° C., preferably in the range from 60° C. to 70° C. This temperature elevation causes contraction of the collagen connective fibers within shaded region 524 of the LES tissue.

The system and method of the present invention may also be useful to efficaciously ablate (i.e., disintegrate) cancer cells and tissue containing cancer cells, such as cancer on the surface of the epidermis, eye, colon, bladder, cervix, uterus and the like. The present invention's ability to completely disintegrate the target tissue can be advantageous in this application because simply vaporizing and fragmenting cancerous tissue may lead to spreading of viable cancer cells (i.e., seeding) to other portions of the patient's body or to the surgical team in close proximity to the target tissue. In addition, the cancerous tissue can be removed to a precise depth while minimizing necrosis of the underlying tissue.

What is claimed is:

1. A method for treating gastroesophageal reflux comprising:
    positioning an electrode terminal adjacent to a tissue structure of the lower sphincter;
    applying high frequency voltage to the electrode terminal, the high frequency voltage being sufficient to volumetrically remove a portion of the tissue structure and to improve the tone of the lower sphincter to reduce reflux; and
    during the applying step, advancing at least a distal end of the electrode terminal into a space vacated by the removed portion of the lower sphincter.

2. The method of claim 1 further comprising applying thermal energy to the tissue structure to form a scar around the space.

3. The method of claim 1 further comprising axially translating the electrode terminal to form a hole through at least a portion of the lower sphincter.

4. The method of claim 1 further comprising transversely translating the electrode terminal relative to the lower sphincter to form a channel along the outer surface of the lower sphincter.

5. The method of claim 1 further comprising positioning the electrode terminal within electrically conductive fluid.

6. The method of claim 5 further comprising applying sufficient voltage to the electrode terminal in the presence of the electrically conducting fluid to vaporize at least a portion of the fluid between the electrode terminal and the tissue structure.

7. The method of claim 6 further comprising accelerating charged particles from the vaporized fluid to the tissue structure to cause dissociation of the molecular bonds within the tissue structure.

* * * * *